United States Patent [19]

Hillman et al.

[11] Patent Number: 5,935,813
[45] Date of Patent: Aug. 10, 1999

[54] HUMAN PANCREATITIS-ASSOCIATED PROTEIN

[75] Inventors: Jennifer L. Hillman, Mountain View; Surya K. Goli, Sunnyvale, both of Calif.

[73] Assignee: Incyte Pharmaceuticals, Inc., Palo Alto, Calif.

[21] Appl. No.: 08/822,261

[22] Filed: Mar. 20, 1997

[51] Int. Cl.⁶ .......................... C12N 15/12; C12N 15/11; C12N 15/00; C07K 14/435

[52] U.S. Cl. .................... 435/69.1; 435/91.2; 435/320.1; 435/252.3; 536/23.1; 536/23.4; 536/23.5; 530/35

[58] Field of Search .................. 536/23.1, 23.4, 536/23.5; 435/69.1, 91.2, 320.1, 252.3; 530/350

[56] References Cited

U.S. PATENT DOCUMENTS 5,436,169  7/1995  Iovanna et al. .

OTHER PUBLICATIONS

Barondes, S.H. et al., "Galectins. Structure and function of a large family of animal lectins." *J.Biol.Chem.* (1994) 269(33):20807–20810.

Stoolman, L.M., "Adhesion Molecules Controlling Lymphocyte Migration," *Cell* 56:907–910 (1989).

Drickamer "Ca²⁺–dependent carbohydrate–rocognition domains in animal proteins." *Curr.Opin.Struct.Biol.* (1993) 3:393–400.

Unno, M. et al., "Structure, chromosomal localization, and expression of mouse reg genes, reg I and reg II." *J.Biol.Chem.* (1993) 268(21):15974–15982.

Terazono, K. et al., "A novel gene activated in regenerating islets." *J.Biol.Chem.* (1988) 263(5):2111–2114.

Moriizumi, S. et al., "Isolation, structural determination and expression of a novel reg gene, human regI β." *Biochim. Biophys.Acta.* (1994) 1217:199–202.

Dusetti, N.J. et al., "Rapid PCR cloning and sequence determination of the rat lithostathine gene." *Biochim.Biophys.Acta.* (1993) 1174:99–102.

Rouquier, S. et al., "Rat Pancreatic Stone Protein Messenger RNA." *J.Biol.Chem.* (1991) 266(2):786–791.

de la Monte, S.M. et al., "Enhanced expression of an exocrine pancreatic protein in Alzheimer's disease and the developing human brain." *J.Clin.Invest.* (1990) 86:1004–1013.

Ozturk, M. et al., "Elevated levels of an exocrine pancreatic secretory protein in Alzheimer disease brain." *Proc.Natl.Acad.Sci.* (1989) 86:419–423.

Iovanna, J. et al., "Messenger RNA sequence and expression of rat pancreatitis–associated protein, a lectin–related protein overexpressed during acute experimental pancreatitis." *J.Biol.Chem.* (1991) 266(36):24664–24669.

Orelle, B. et al., "Human pancreatitis–associated protein. Messenger RNA cloning and expression in pancreatic diseases." *J.Clin.Invest.* (1992) 90:2284–2291.

Itoh, T. et al., "Cloning and tissue–specific expression of cDNAs for the human and mouse homologues of rat pancreatitis–associated protein (PAP)." *Biochim.Biophys.Acta.* (1993) 1172:184–186.

Dusetti, N.J. et al., "Molecular cloning, genomic organization, and chromosomal localization of the human pancreatitis–associated protein (PAP) gene." *Genomics* (1994) 19:108–114.

Keim, V. et al., "Characterization of a rat pancreatic secretory protein associated with pancreatitis." *Gastroenterology* (1991) 100:775–782.

Christa, L. et al., "The human HIP gene overexpressed in primary liver cancer encodes for a C–type carbohydrate binding protein with lactose binding activity." *FEBS Letters* (1994) 337:114–118.

Lasserre, C. et al., "A novel gene (HIP) activated in human primary liver cancer." *Cancer Res.* (1992) 52:5089–5095.

Orelle, B. et al. (GI 262369), GenBank Sequence Database (Accession S51768), National Center for Biotechnology Information, National Library of Medicine, Bethesda, Maryland, 20894.

Orelle, B. et al. (GI 262368), GenBank Sequence Database (Accession S51768), National Center for Biotechnology Information, National Library of Medicine, Bethesda, Maryland, 20894.

*Primary Examiner*—Paula K. Hutzell
*Assistant Examiner*—Khalid Masood
*Attorney, Agent, or Firm*—Leanne C. Price; Incyte Pharmaceuticals, Inc.

[57] ABSTRACT

The present invention provides a novel human C-type lectin (human PAP-2) and polynucleotides which identify and encode human PAP-2. The invention also provides expression vectors, host cells, agonists, antibodies or antagonists. The invention also provides methods for treating or preventing diseases associated with expression of human PAP-2.

8 Claims, 6 Drawing Sheets

```
                9              18              27              36              45              54
5' NAG TCC TAG GGG ACT ACA GAA GGA AAA AGA CAA GAG GCA GTA GGA TAT CTG TGT
                63              72              81              90              99             108
   GTC CTC CCG CTG ACC ACA CTT CCT TTA GTG ACC CGA TTG CCT CAA GTC GCA
                117             126             135             144             153             162
   GAC ACT ATG CTG CCT CCC ATG GCC CTG CCC AGT GTG TCC TGG ATG CTG CTT TCC
        M   L   P   P   M   A   L   P   S   V   S   W   M   L   L   S
                171             180             189             198             207             216
   TGC CTC ATT CTC CTG TGT CAG GTT CAA GGT GAA ACC CAG AAG GAA CTG CCC
    C   L   I   L   L   C   Q   V   Q   G   E   T   Q   K   E   L   P
                225             234             243             252             261             270
   TCT CCA CGG ATC AGC TGT CCC AAA GGC TCC AAG GCC TAT GGC TCC CCC TGC TAT
    S   P   R   I   S   C   P   K   G   S   K   A   Y   G   S   P   C   Y
                279             288             297             306             315             324
   GCC TTG TTT TTG TCA CCA AAA TCC TGG ATG GAT GCA GAT CTG GCT TGC CAG AAG
    A   L   F   L   S   P   K   S   W   M   D   A   D   L   A   C   Q   K
                333             342             351             360             369             378
   CGG CCC TCT GGA AAA CTG GTG TCT CTC AGT GGG GCT GAG GGA GGA TCC TTC GTG
    R   P   S   G   K   L   V   S   L   S   G   A   E   G   G   S   F   V
```

FIGURE 1A

```
                387     396     405     414     423     432
TCC TCC CTG GTG AGG AGC ATT AGT AAC AGC TAC ATC TGG ATT GGG CTC
 S   S   L   V   R   S   I   S   N   S   Y   I   W   I   G   L 441     450     459     468     477     486
CAT GAC CCC ACA CAG GGC TCT GAG CCT GAT GGA TGG GAG TGG AGT AGC
 H   D   P   T   Q   G   S   E   P   D   G   W   E   W   S   S 495     504     513     522     531     540
ACT GAT GTG ATG AAT TAC TTT GCA TGG GAG AAA AAT CCC TCC ACC ATC TTA AAC
 T   D   V   M   N   Y   F   A   W   E   K   N   P   S   T   I   L   N 549     558     567     576     585     594
CCT GGC CAC TGT GGG AGC CTG TCA AGA AGC ACA GGA TTT CTG AAG TGG AAA GAT
 P   G   H   C   G   S   L   S   R   S   T   G   F   L   K   W   K   D 603     612     621     630     639     648
TAT AAC TGT GAT GCA AAG TTA CCC TAT GTC TGC AAG TTC AAG TTC AAG GAC TAG GGC AGG
 Y   N   C   D   A   K   L   P   Y   V   C   K   F   K   D 657     666     675     684     693     702
TGG GAA GTC AGC AGC CTC AGC TTG GCG TGC AGC TCA TCA TGG ACA TGA GAC CAG 711     720     729     738     747     756
TGT GAC TCA CCC TGG AAG AGA ATA TTC TCC CCA AAC TGC CCT ACC TGA CTA

CCT TGT A 3'
```

| Library | Lib Description | Abun | Pct Abun |
|---|---|---|---|
| PANCNOT01 | pancreas, 29 M | 157 | 3.3576 |
| SININOT01 | small intestine, ileum, 4 F | 32 | 0.8956 |
| SINTNOT02 | small intestine, 55 F | 17 | 0.5878 |
| ISLTNOT01 | pancreas, islet cells, M/F | 86 | 0.5535 |
| PANCDIT03 | pancreas, Type II diabetes, 57 M | 2 | 0.2924 |
| SINTBST01 | small intestine, ileum, Crohn's, 18 F | 12 | 0.2019 |
| COLSUCT01 | colon, sigmoid, ulcerative colitis, 70 M | 4 | 0.1635 |
| PANCTUT02 | pancreatic tumor, carcinoma, 45 F | 18 | 0.1551 |
| ESOGTUT02 | esophageal tumor, adenocarcinoma, 61 M | 5 | 0.1196 |
| COLNNOT19 | large intestine, cecum, 18 F | 4 | 0.1171 |
| TESTNOT04 | testis, 37 M | 1 | 0.1075 |
| PANCNOT04 | pancreas, 5 M | 5 | 0.0844 |
| LUNGTUT09 | lung tumor, 68 M | 2 | 0.0506 |
| PANCNOT05 | pancreas, 2 M | 3 | 0.0437 |
| COLNTUT06 | large intestine, cecal tumor, 45 F | 1 | 0.0293 |
| SINTNOT13 | small intestine, ulcerative colitis, 25 F | 1 | 0.0275 |
| COLANOT02 | ascending colon, ulcerative colitis, 25 F | 1 | 0.0251 |
| COLNTUT02 | colon tumor, 75 M, match to COLNNOT01 | 1 | 0.0220 |
| PLACNOT02 | placenta, fetal F | 1 | 0.0168 |
| TESTNOT03 | testis, 37 M | 1 | 0.0129 |

FIGURE 4

HUMAN PANCREATITIS-ASSOCIATED PROTEIN

FIELD OF THE INVENTION

The present invention relates to nucleic acid and amino acid sequences of a novel human pancreatitis-associated (PAP) protein, which comprises a soluble C-type lectin. This novel human PAP protein shares features with other proteins in the reg/PSP multigene family which are involved in the regulation of cell growth. The present invention relates to the use of these novel sequences in the diagnosis, prevention and treatment of disease.

BACKGROUND OF THE INVENTION

Lectins are proteins which are defined by their ability to bind carbohydrates specifically and to agglutinate cells. Lectins have been shown to be involved in a wide variety of cellular functions including cell-cell and cell-matrix interactions. Lectins are widespread among plants, invertebrates and mammals.

Animal lectins have been grouped into four distinct families: 1) C-type lectins, which include selectins; 2) P-type lectins; 3) galectins (formerly termed S-type lectins or S-Lac lectins); and 4) pentraxins [Barondes SH et al. (1994) J. Biol. Chem. 269:20807–10]. The C-type lectins bind carbohydrate ligands in a $Ca^{2+}$-dependent manner and are structurally related to the asialoglycoprotein receptor. Selectins, a subcategory of the C-type lectins, are composite transmembrane molecules which are involved in cell-cell interactions. The selectins include lymphocyte homing receptors and platelet/endothelial cell surface receptors [Stoolman (1989) Cell 56:907–10].

C-type animal lectins contain $Ca^{2+}$-dependent carbohydrate-recognition domains (CRDs). The prototypical C-type animal lectins are integral membrane proteins (e.g., the asialoglycoprotein receptor); however, a number of soluble C-type animal lectins have been identified. One group of soluble C-type animal lectins, termed collectins or Group III C-type lectins, comprise proteins having both lectin- (i.e., CRD) and collagenous-like domains within a single polypeptide [Drickamer (1993) Curr. Opin. Struct. Biol. 3:393]. Another group of soluble C-type animal lectins, termed Group IV C-type lectins, comprise free CRDs which are not joined to other polypeptide domains (other than a signal peptide utilized in secretion) [Drickamer (1993), supra]. The soluble C-type animal lectins comprising free CRDs found in mammals are most closely related to proteins identified in invertebrates and lower vertebrates (e.g., snakes).

Proteins recognized as members of the Group IV C-type lectins appear to be members of a multigene family termed the reg/PSP multigene family [Drickamer (1993), supra and Unno et al. (1993) J. Biol. Chem. 268:15974]. The reg/PSP multigene family comprises genes encoding secretory proteins which are expressed in the pancreas; the ectopic expression (i.e., expression in a tissue which does not normally express reg/PSP proteins) of some members of the reg/PSP family is associated with disease states such as tumors and Alzheimer's disease.

The first member of the reg/PSP multigene family was identified in a cDNA library derived from rat regenerating pancreatic islets [Terazono et al. (1988) J. Biol. Chem. 263:2111]. This gene was termed reg (regenerating gene) and is now known as the regIα gene. The regIα gene product has been called by different investigators reg protein, regIα protein, lithostathine, islet cell regeneration factor (ICRF), pancreatic stone protein (PSP) and pancreatic thread protein (PTP) [Terazono et al. (1988), supra; Moriizumi et al. (1994) Biochem. Biophys. Acta 1217:199; Dusetti et al. (1993) Biochem. Biophys. Acta 1174:99; Rouquier et al. (1991) J. Biol. Chem. 266:786; and de la Monte et al. (1990) J. Clin. Invest. 86:1004]. The clear association between reg gene expression and islet cell replication in vitro has lead to the suggestion that the regIα/lithostathine protein has a growth-promoting activity for islet β-cells [Unno et al. (1993), supra]. Human regIα mRNA is expressed in colon and rectal tumors although it is not expressed in normal colon or rectal tissue. Thus, ectopic expression of regIα protein is associated with tumorigenesis. Elevated levels of regIα protein has been found in the brains of patients suffering from Alzheimer's disease as well as in the brains of middle-aged individuals with Down's syndrome [Ozturk et al. (1989) Proc. Natl. Acad. Sci. USA 86:419 and de la Monte et al. (1990) J. Clin. Invest. 86:1004]. RegIα MRNA is expressed in the developing human brain, but not in normal adult brain; expression of regIα is seen in adult brain which undergoing regenerative sprouting. Given its pattern of expression (e.g., expression in regenerating pancreatic islets and brain, expression in tumors), it appears that regIα protein is associated with cell growth.

Other members of the reg/PSP multigene family are the genes encoding pancreatitis-associated proteins (PAPs) which have been identified in humans, mice and rats [Iovanna et al. (1991) J. Biol. Chem. 266:24664; Orelle et al. (1992) J. Clin. Invest. 90:2284; Itoh and Teraoka (1993) Biochem. Biophys. Acta 1172:184; and Dusetti et al. (1994) Genomics 19:108]. The reg/lithostathine and PAP proteins characterized to date share about 45–65% identity on the amino acid level.

The PAP proteins are secretory proteins which are stored in zymogen granules prior to secretion [Keim et al. (1991) Gastroenterol. 100:775]; PAP is present at low levels in normal pancreas but is rapidly overexpressed during the acute phase of pancreatitis. PAP, like other members of the reg/PSP family, shares sequence similarity with the carbohydrate-binding domain of C-type lectins which likely explains the ability of PAP to induce aggregation of bacteria [Iovanna et al. (1991), supra]. The ability to aggregate bacteria has lead to the suggestion that PAP is involved in the control of bacterial proliferation, a frequent complication of pancreatitis. PAP has been shown to be able to bind lactose [Christa et al. (1994) FEBS Lett. 337:114].

Three PAP genes, PAP I–III, have been identified in rats. All three PAP genes are expressed during the acute phase of pancreatitis. Rat PAP I and PAP III are expressed constitutively in the intestine and their expression is induced by feeding. Rat PAP II is not expressed in the intestine. Rat PAP I and PAP III share 66% amino acid identity; rat PAP II and PAP III share 63% amino acid identity; rat PAP I and PAP II share 58% amino acid identity. A homologue of rat PAP I has been identified in cows [BPTP; de la Monte et al. (1990), supra].

A human homolog of the rat PAP I gene, human PAP or human PAP I, has been identified [Orelle et al. (1992) J. Clin. Invest. 90:2284]. The human PAP I protein is the same size as the rat PAP I protein (175 amino acids) and these two proteins share 71% amino acid identity, including conservation of 7 cystine residues. Both the rat and the human PAP I proteins are synthesized as preproteins having an N-terminal signal peptide of 26 amino acids. Expression of the human PAP I mRNA is increased in necrohemorragic pancreatitis. Serum levels of human PAP I were found to be near background levels in normal individuals; in individuals suffering from acute pancreatitis or acute exacerbations of chronic pancreatitis, human PAP I levels increased 24–140 times the background level [Orelle et al. (1992), supra]. Thus, human PAP I appears to serve as a marker of acute pancreatitis.

The human PAP I gene is also referred to as the HIP gene [Lasserre et al. (1992) Cancer Res. 52:5089]. The HIP gene was identified by differential screening of a human primary liver cancer (hepatocellular carcinoma) library. The human PAP I/HIP gene is not expressed in normal adult or fetal liver; expression of PAP I/HIP is limited to the pancreas and small intestine in normal tissues. Thus, the ectopic expression of PAP I/HIP is associated with tumorigenesis in the liver. In addition, PAP I/HIP MRNA is expressed in human pancreatic cell hyperplasia (hyperinsulinism) (Lasserre et al., supra).

Proteins expressed by the reg/PSP multigene family represent an important family of proteins which are involved in maintenance of proper pancreatic function as well as in the regulation of cell proliferation and/or differentiation. Discovery of new molecules related to or in the mammalian reg/PSP multigene family is useful for the development of new diagnostic or therapeutic compositions.

SUMMARY OF THE INVENTION

The present invention features a novel Group IV C-type lectin protein hereinafter designated human PAP-2 and characterized as having similarity to the human PAP 1 protein. Human PAP-2 is a member of the PAP branch of the reg/PSP multigene family.

Accordingly, the invention features a substantially purified polypeptide having the amino acid sequence shown in SEQ ID NO:1 or fragments thereof. Preferred fragments of SEQ ID NO:1 are fragments which retain biological activity or immunological activity (i.e., capable of eliciting anti-human PAP-2 antibodies). Fragments of SEQ ID NO:1 which are at least 15 amino acids, at least 50 amino acids, at least 100 amino acids, at least 125 amino acids and at least 200 amino acids in length are contemplated. The invention specifically contemplates secretory (i.e., the signal peptide is cleaved; $E_{27}$-$D_{175}$ of SEQ ID NO:1) and nonsecretory (i.e., signal peptide remains) forms of a substantially purified human PAP-2 as well as any proteolytic fragments thereof.

The present invention further provides isolated and substantially purified polynucleotide sequences encoding the polypeptide comprising the amino acid sequence of SEQ ID NO:1 or fragments thereof. In a particular aspect, the polynucleotide is the nucleotide sequence of SEQ ID NO:2 or variants thereof. In another embodiment, the present invention provides polynucleotides comprising fragments of SEQ ID NO:2 having a length of at least seven nucleotides. The invention further contemplates fragments of this polynucleotide sequence (i.e., SEQ ID NO:2) that are at least 50 nucleotides, at least 100 nucleotides, at least 250 nucleotides, at least 500 nucleotides and at least 750 nucleotides in length.

In addition, the invention provides polynucleotide sequences which hybridize under stringent conditions to the polynucleotide sequence of SEQ ID NO:2. In another embodiment the present invention provides a composition comprising an isolated and purified polynucleotide sequence encoding human PAP-2.

The invention provides polynucleotide sequences comprising the complement of SEQ ID NO:2 or variants thereof; these complementary nucleic acid sequences may comprise the complement of the entire nucleic acid sequence of SEQ ID NO:2 or fragments thereof. In another embodiment the present invention provides a composition comprising an isolated and purified polynucleotide sequence comprising the complement of SEQ ID NO:2 or variants thereof.

The invention additionally features nucleic acid sequences encoding polypeptides, oligonucleotides, peptide nucleic acids (PNA), fragments, portions or antisense molecules thereof, and expression vectors and host cells comprising polynucleotides that encode human PAP-2.

In another embodiment the present invention provides an isolated polynucleotide comprising at least a portion of the nucleic acid sequence of SEQ ID NO:2 or variants thereof contained on a recombinant expression vector. In yet another embodiment, the expression vector containing the polynucleotide sequence is contained within a host cell. The invention is not limited by the nature of the host cell employed. For example, the host cell may be an *E. coli* cell, a yeast cell, an insect cell, a mammalian cell, etc.

The present invention also provides a method for producing a polypeptide comprising the amino acid sequence of SEQ ID NO:1 or fragments thereof, the method comprising the steps of:, a) culturing the host cell containing an expression vector containing an isolated polynucleotide encoding at least a fragment of the human PAP-2 polypeptide under conditions suitable for the expression of the polypeptide; and b) recovering the polypeptide from the host cell culture.

In another embodiment, the invention provides a pharmaceutical composition comprising a substantially purified human PAP-2 protein having the amino acid sequence of SEQ ID NO:1 in conjunction with a suitable pharmaceutical carrier.

The invention also provides a purified antibody which binds specifically to a polypeptide comprising at least a portion of the amino acid sequence of SEQ ID NO:1.

Still further, the invention provides a purified agonist which specifically binds to and modulates the activity of a polypeptide comprising at least a portion of the amino acid sequence of SEQ ID NO:1. The present invention further provides a pharmaceutical composition comprising a purified agonist which specifically binds to and modulates the activity of a polypeptide comprising at least a portion of the amino acid sequence of SEQ ID NO:1. In another embodiment, the invention provides a purified antagonist which specifically binds to and modulates the activity of a polypeptide comprising at least a portion of the amino acid sequence of SEQ ID NO:1. The present invention further provides a pharmaceutical composition comprising a purified antagonist which specifically binds to and modulates the activity of a polypeptide comprising at least a portion of the amino acid sequence of SEQ ID NO:1.

The invention also provides a method for treating pancreatitis (particularly for preventing or controlling bacterial infections associated with pancreatitis) comprising administering to a subject in need of such treatment an effective amount of a pharmnaceutical composition comprising a purified agonist which specifically binds to and modulates the activity of a polypeptide comprising at least a portion of the amino acid sequence of SEQ ID NO:1. The treatment of a variety of tumors, including but not limited to tumors of the pancreas, esophagus lung and large intestine (e.g., cecum and colon), using agonists as well as antagonists of human PAP-2 is also contemplated by the present invention.

The invention also provides a method for detection of polynucleotides encoding human PAP-2 in a biological sample comprising the steps of: a) hybridizing a polynucleotide sequence encoding human PAP-2 (SEQ ID NO:1) to nucleic acid material of a biological sample, thereby forming a hybridization complex; and b) detecting the hybridization complex, wherein the presence of the complex correlates with the presence of a polynucleotide encoding human PAP-2 in the biological sample. In a preferred embodiment, prior to hybridization, the nucleic acid material of the biological sample is amplified by the polymerase chain reaction.

BRIEF DESCRIPTION OF THE FIGURES

FIGS. 1A and 1B shows the amino acid sequence (SEQ ID NO:1) and nucleic acid sequence (SEQ ID NO:2) of human PAP-2. The alignment was produced using MacDNASIS PRO™ software (Hitachi Software Engineering Co., Ltd., San Bruno. Calif.).

FIG. 2 shows the amino acid sequence alignments among the human PAP-2 protein (SEQ ID NO:1) and human PAP 1 proteins (GI 262369; SEQ ID NO:3 and GI 189601; SEQ ID NO:4). The alignment was produced using the multisequence alignment program of DNASTAR™ software (DNASTAR Inc, Madison Wis.).

FIG. 4 shows the northern analysis for SEQ ID NO:2. The northern analysis was produced electronically using LIFESEQ™ database (Incyte Pharmaceuticals, Inc., Palo Alto, Calif.).

DESCRIPTION OF THE INVENTION

Figure 3A:
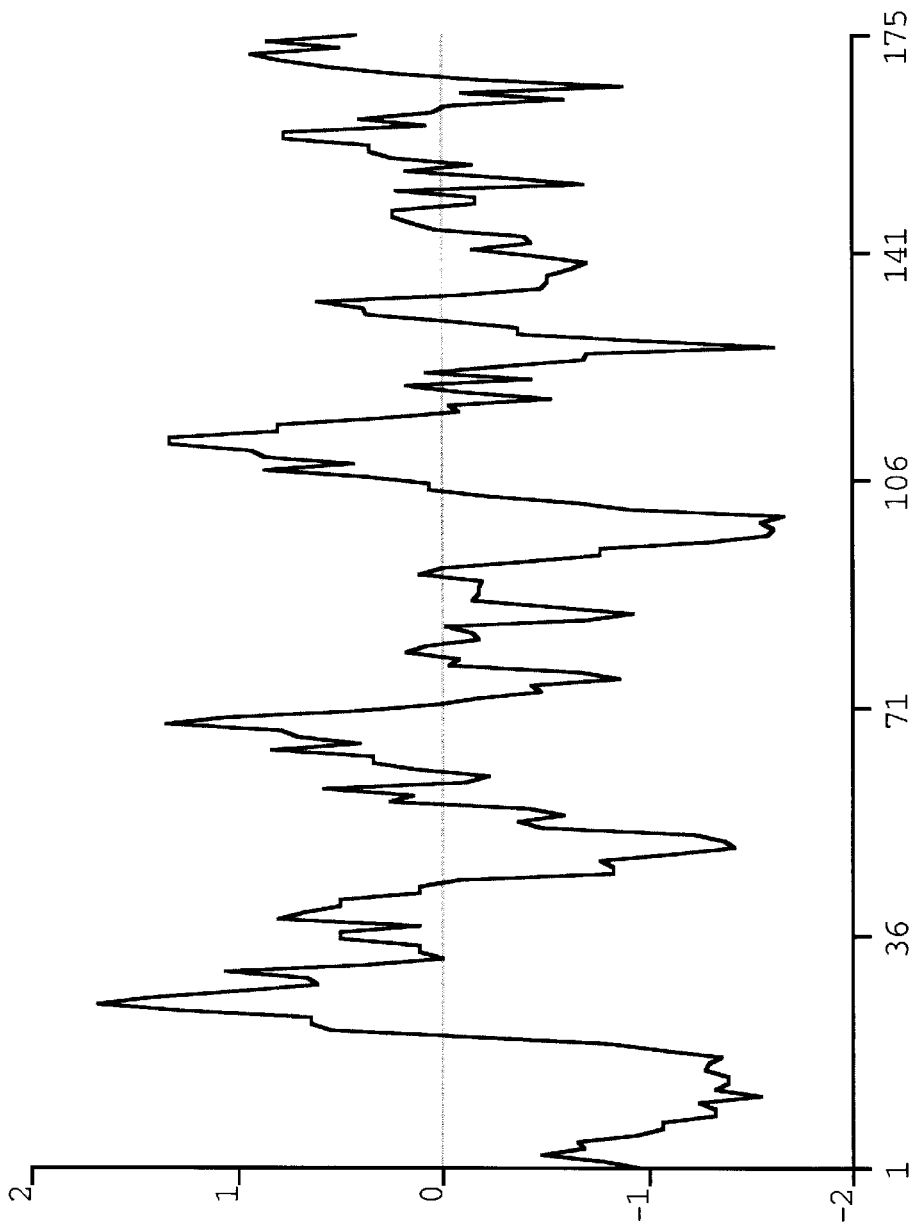
FIGS. 3A and 3B shows the hydrophobicity plot (MacDNASIS PRO software) for human PAP-2, SEQ ID NO:1 and human PAP I, SEQ ID NO:3, respectively; the positive X axis reflects amino acid position, and the negative Y axis, hydrophobicity.

Before the present proteins, nucleotide sequences, and methods are described, it is understood that this invention is not limited to the particular methodology, protocols, cell lines, vectors, and reagents described as these may vary. It is also to be understood that the terminology used herein is for the purpose of describing particular embodiments only, and is not intended to limit the scope of the present invention which will be limited only by the appended claims.

It must be noted that as used herein and in the appended claims, the singular forms "a", "an", and "the" include plural reference unless the context clearly dictates otherwise. Thus, for example, reference to "a host cell" includes a plurality of such host cells, reference to the "antibody" is a reference to one or more antibodies and equivalents thereof known to those skilled in the art, and so forth.

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods, devices, and materials are now described. All publications mentioned herein are incorporated herein by reference for the purpose of describing and disclosing the cell lines, vectors, and methodologies which are reported in the publications which might be used in connection with the invention. Nothing herein is to be construed as an admission that the invention is not entitled to antedate such disclosure by virtue of prior invention.

DEFINITIONS

"Nucleic acid sequence" as used herein refers to an oligonucleotide, nucleotide, or polynucleotide, and fragments or portions thereof, and to DNA or RNA of genomic or synthetic origin which may be single- or double-stranded, and represent the sense or antisense strand. Similarly, "amino acid sequence" as used herein refers to an oligopeptide, peptide, polypeptide, or protein sequence, and fragments or portions thereof, and to naturally occurring or synthetic molecules.

A "composition comprising a given polynucleotide sequence" as used herein refers broadly to any composition containing the given polynucleotide sequence. The composition may comprise an aqueous solution. Compositions comprising polynucleotide sequences encoding human PAP-2 (SEQ ID NO:1) or fragments thereof (e.g., SEQ ID NO:2 and fragments thereof) may be employed as hybridization probes. In this case, the human PAP-2-encoding nucleotide sequences are typically employed in an aqueous solution containing salts (e.g., NaCl), detergents (e.g., SDS) and other components (e.g., Denhardt's solution, dry milk, salmon sperm DNA, etc.).

Where "amino acid sequence" is recited herein to refer to an amino acid sequence of a naturally occurring protein molecule, "amino acid sequence" and like terms, such as "polypeptide" or "protein" are not meant to limit the amino acid sequence to the complete, native amino acid sequence associated with the recited protein molecule.

"Peptide nucleic acid", as used herein, refers to a molecule which comprises an oligomer to which an amino acid residue, such as lysine, and an amino group have been added. These small molecules, also designated anti-gene agents, stop transcript elongation by binding to their complementary strand of nucleic acid (Nielsen, P. E. et al. (1993) Anticancer Drug Des. 8:53–63).

As used herein the "reg/PSP multigene family" refers to genes encoding any of the following proteins: regenerating protein, reg protein, regIα protein, regIβ, lithostathine, islet cell regeneration factor (ICRF), pancreatic stone protein (PSP), pancreatic thread protein (PTP), HIP protein, pancreatitis-associated protein (PAP) and the novel human PAP-2 of the present invention, as well as other genes which encode proteins sharing at least 21% identity with the listed proteins. Members of the reg/PSP multigene family share a number of features including expression in the pancreas and the presence of sequences conserved among the CRD of C-type lectins. On the amino acid level, members of the reg/PSP multigene family share about 30–87% identity. Protein sequences comprising typical amino acid compositions (i.e., amino acids are present at their observed normal frequencies) which share an identity of greater than 20% are defined as "homologous" or related proteins; this assumes that only a limited number of insertions and deletions are made to align the sequences being compared [Creighton, *Proteins, Structure and Molecular Properties*, 2nd ed., W. H. Freeman, N.Y., pp. 108–109 (1993)].

Human PAP-2, as used herein, refers to the amino acid sequences of substantially purified human PAP-2 obtained from any species, particularly mammalian, including bovine, ovine, porcine, murine, equine, and preferably human, from any source whether natural, synthetic, semisynthetic, or recombinant.

"Consensus", as used herein, refers to a nucleic acid sequence which has been resequenced to resolve uncalled bases, or which has been extended using XL-PCR™ (Perkin Elmer, Norwalk, Conn.) in the 5' and/or the 3' direction and resequenced, or which has been assembled from the overlapping sequences of more than one Incyte clone using the GELVIEW™ Fragment Assembly system (GCG, Madison, Wis.), or which has been both extended and assembled.

A "variant" of human PAP-2, as used herein, refers to an amino acid sequence that is altered by one or more amino acids. The variant may have "conservative" changes, wherein a substituted amino acid has similar structural or chemical properties, e.g., replacement of leucine with isoleucine. More rarely, a variant may have "nonconservative" changes, e.g., replacement of a glycine with a tryptophan. Similar minor variations may also include amino acid deletions or insertions, or both. Guidance in determining which amino acid residues may be substituted, inserted, or deleted without abolishing biological or immunological activity may be found using computer programs well known in the art, for example, DNASTAR software.

A "deletion", as used herein, refers to a change in either amino acid or nucleotide sequence in which one or more amino acid or nucleotide residues, respectively, are absent.

An "insertion" or "addition", as used herein, refers to a change in an amino acid or nucleotide sequence resulting in the addition of one or more amino acid or nucleotide residues, respectively, as compared to the naturally occurring molecule.

A "substitution", as used herein, refers to the replacement of one or more amino acids or nucleotides by different amino acids or nucleotides, respectively.

The term "biologically active", as used herein, refers to a protein having structural, regulatory, or biochemical functions of a naturally occurring molecule. Likewise, "immunologically active" refers to the capability of the natural, recombinant, or synthetic human PAP-2, or any oligopeptide thereof, to induce a specific immune response in appropriate animals or cells and to bind with specific antibodies.

The term "agonist", as used herein, refers to a molecule which, when bound to human PAP-2, causes a change in human PAP-2 which modulates the activity of human PAP-2. Agonists may include proteins, nucleic acids, carbohydrates, or any other molecules which bind to human PAP-2.

The terms "antagonist" or "inhibitor", as used herein, refer to a molecule which, when bound to human PAP-2, blocks or modulates the biological or immunological activity of human PAP-2. Antagonists and inhibitors may include proteins, nucleic acids, carbohydrates, or any other molecules which bind to human PAP-2.

The term "modulate", as used herein, refers to a change or an alteration in the biological activity of human PAP-2. Modulation may be an increase or a decrease in protein activity, a change in binding characteristics, or any other change in the biological, functional, or immunological properties of human PAP-2.

The term "mimetic", as used herein, refers to a molecule, the structure of which is developed from knowledge of the structure of human PAP-2 or portions thereof and, as such, is able to effect some or all of the actions of human PAP-2-like molecules.

The term "derivative", as used herein, refers to the chemical modification of a nucleic acid encoding human PAP-2 or the encoded human PAP-2. Illustrative of such modifications would be replacement of hydrogen by an alkyl, acyl, or amino group. A nucleic acid derivative would encode a polypeptide which retains essential biological characteristics of the natural molecule.

The term "substantially purified", as used herein, refers to nucleic or amino acid sequences that are removed from their natural environment, isolated or separated, and are at least 60% free, preferably 75% free, and most preferably 90% free from other components with which they are naturally associated. "Amplification" as used herein refers to the production of additional copies of a nucleic acid sequence and is generally carried out using polymerase chain reaction (PCR) technologies well known in the art (Dieffenbach, C. W. and G. S. Dveksler (1995) *PCR Primer, a Laboratory Manual*, Cold Spring Harbor Press, Plainview, N.Y.).

The term "hybridization", as used herein, refers to any process by which a strand of nucleic acid binds with a complementary strand through base pairing.

The term "hybridization complex", as used herein, refers to a complex formed between two nucleic acid sequences by virtue of the formation of hydrogen binds between complementary G and C bases and between complementary A and T bases; these hydrogen bonds may be further stabilized by base stacking interactions. The two complementary nucleic acid sequences hydrogen bond in an antiparallel configuration. A hybridization complex may be formed in solution (e.g., $C_0t$ or $R_0t$ analysis) or between one nucleic acid sequence present in solution and another nucleic acid sequence immobilized on a solid support (e.g., membranes, filters, chips, pins or glass slides to which cells have been fixed for in situ hybridization).

The terms "complementary" or "complementarity", as used herein, refer to the natural binding of polynucleotides under permissive salt and temperature conditions by base-pairing. For example, for the sequence "A-G-T" binds to the complementary sequence "T-C-A". Complementarity between two single-stranded molecules may be "partial", in which only some of the nucleic acids bind, or it may be complete when total complementarity exists between the single stranded molecules. The degree of complementarity between nucleic acid strands has significant effects on the efficiency and strength of hybridization between nucleic acid strands. This is of particular importance in amplification reactions, which depend upon binding between nucleic acids strands.

The term "homology", as used herein, refers to a degree of complementarity. There may be partial homology or complete homology (i.e., identity). A partially complementary sequence is one that at least partially inhibits an identical sequence from hybridizing to a target nucleic acid; it is referred to using the functional term "substantially homologous." The inhibition of hybridization of the completely complementary sequence to the target sequence may be examined using a hybridization assay (Southern or northern blot, solution hybridization and the like) under conditions of low stringency. A substantially homologous sequence or probe will compete for and inhibit the binding (i.e., the hybridization) of a completely homologous sequence or probe to the target sequence under conditions of low stringency. This is not to say that conditions of low stringency are such that non-specific binding is permitted; low stringency conditions require that the binding of two sequences to one another be a specific (i.e., selective) interaction. The absence of non-specific binding may be tested by the use of a second target sequence which lacks even a partial degree of complementarity (e.g., less than about 30% identity); in the absence of non-specific binding, the probe will not hybridize to the second non-complementary target sequence.

As known in the art, numerous equivalent conditions may be employed to comprise either low or high stringency conditions. Factors such as the length and nature (DNA, RNA, base composition) of the sequence, nature of the target (DNA, RNA, base composition, presence in solution or immobilization, etc.), and the concentration of the salts and other components (e.g., the presence or absence of formamide, dextran sulfate and/or polyethylene glycol) are considered and the hybridization solution may be varied to generate conditions of either low or high stringency different from, but equivalent to, the above listed conditions.

The term "stringent conditions", as used herein, is the "stringency" which occurs within a range from about Tm-5° C. (5° C. below the melting temperature (Tm) of the probe) to about 20° C. to 25° C. below Tm. As will be understood by those of skill in the art, the stringency of hybridization may be altered in order to identify or detect identical or related polynucleotide sequences. Under "stringent conditions" SEQ ID NO:2 or fragments thereof will hybridize to its exact complement and closely related sequences. The stringent conditions are chosen such that SEQ ID NO:2 or fragments thereof will hybridize to sequences encoding human PAP-2 but not to sequences encoding human PAP I proteins (i.e., SEQ ID NOs:5 and 6 or their RNA equivalents). When fragments of SEQ ID NO:2 are employed in hybridization reactions, the stringent conditions include the choice of fragments of SEQ ID NO:2 to be used. Fragments of SEQ ID NO:2 which contain unique sequences (i.e., regions which are either non-homologous to or which contain less than about 50% homology or complementarity with SEQ ID NOS:4 and/or 6 are preferentially employed. SEQ ID NOS:5 and 6 represent DNA sequences encoding human PAP I proteins; these DNA sequences can be found in GenBank under GI 262368 (SEQ ID NO:5) and GI 189600 (SEQ ID NO:6), respectively.

The term "antisense", as used herein, refers to nucleotide sequences which are complementary to a specific DNA or RNA sequence. The term "antisense strand" is used in reference to a nucleic acid strand that is complementary to the "sense" strand. Antisense molecules may be produced by any method, including synthesis by ligating the gene(s) of interest in a reverse orientation to a viral promoter which permits the synthesis of a complementary strand. Once introduced into a cell, this transcribed strand combines with natural sequences produced by the cell to form duplexes. These duplexes then block either the further transcription or translation. In this manner, mutant phenotypes may be generated. The designation "negative" is sometimes used in reference to the antisense strand, and "positive" is sometimes used in reference to the sense strand.

The term "portion", as used herein, with regard to a protein (as in "a portion of a given protein") refers to fragments of that protein. The fragments may range in size from four amino acid residues to the entire amino acid sequence minus one amino acid. Thus, a protein "comprising at least a portion of the amino acid sequence of SEQ ID NO:1" encompasses the full-length human PAP-2 and fragments thereof.

"Transformation", as defined herein, describes a process by which exogenous DNA enters and changes a recipient cell. It may occur under natural or artificial conditions using various methods well known in the art. Transformation may rely on any known method for the insertion of foreign nucleic acid sequences into a prokaryotic or eukaryotic host cell. The method is selected based on the host cell being transformed and may include, but is not limited to, viral infection, electroporation, lipofection, and particle bombardment. Such "transformed" cells include stably transformed cells in which the inserted DNA is capable of replication either as an autonomously replicating plasmid or as part of the host chromosome. They also include cells which transiently express the inserted DNA or RNA for limited periods of time.

The term "antigenic determinant", as used herein, refers to that portion of a molecule that makes contact with a particular antibody (i.e., an epitope). When a protein or fragment of a protein is used to immunize a host animal, numerous regions of the protein may induce the production of antibodies which bind specifically to a given region or three-dimensional structure on the protein; these regions or structures are referred to as antigenic determinants. An antigenic determinant may compete with the intact antigen (i.e., the immunogen used to elicit the immune response) for binding to an antibody.

The terms "specific binding" or "specifically binding", as used herein, in reference to the interaction of an antibody and a protein or peptide, mean that the interaction is dependent upon the presence of a particular structure (i.e., the antigenic determinant or epitope) on the protein; in other words, the antibody is recognizing and binding to a specific protein structure rather than to proteins in general. For example, if an antibody is specific for epitope "A", the presence of a protein containing epitope A (or free, unlabeled A) in a reaction containing labeled "A" and the antibody will reduce the amount of labeled A bound to the antibody.

The term "sample", as used herein, is used in its broadest sense. A biological sample suspected of containing nucleic acid encoding human PAP-2 or fragments thereof may comprise a cell, chromosomes isolated from a cell (e.g., a spread of metaphase chromosomes), genomic DNA (in solution or bound to a solid support such as for Southern analysis), RNA (in solution or bound to a solid support such as for northern analysis), cDNA (in solution or bound to a solid support), an extract from cells or a tissue, and the like.

The term "correlates with expression of a polynucleotide", as used herein, indicates that the detection of the presence of ribonucleic acid that is similar to SEQ ID NO:2 by northern analysis is indicative of the presence of mRNA encoding human PAP-2 in a sample and thereby correlates with expression of the transcript from the polynucleotide encoding the protein.

"Alterations" in the polynucleotide of SEQ ID NO:2, as used herein, comprise any alteration in the sequence of polynucleotides encoding human PAP-2 including deletions, insertions, and point mutations that may be detected using hybridization assays. Included within this definition is the detection of alterations to the genomic DNA sequence which encodes human PAP-2 (e.g., by alterations in the pattern of restriction fragment length polymorphisms capable of hybridizing to SEQ ID NO:2), the inability of a selected fragment of SEQ ID NO:2 to hybridize to a sample of genomic DNA (e.g., using allele-specific oligonucleotide probes), and improper or unexpected hybridization, such as hybridization to a locus other than the normal chromosomal locus for the polynucleotide sequence encoding human PAP-2 (e.g., using fluorescent in situ hybridization [FISH] to metaphase chromosomes spreads).

As used herein, the term "antibody" refers to intact molecules as well as fragments thereof, such as Fa, F(ab')$_2$, and Fv, which are capable of binding the epitopic determinant. Antibodies that bind human PAP-2 polypeptides can be prepared using intact polypeptides or fragments containing small peptides of interest as the immunizing antigen. The polypeptide or peptide used to immunize an animal can be derived from the transition of RNA or synthesized chemically, and can be conjugated to a carrier protein, if desired. Commonly used carriers that are chemically coupled to peptides include bovine serum albumin and thyroglobulin. The coupled peptide is then used to immunize the animal (e.g., a mouse, a rat, or a rabbit).

The term "humanized antibody", as used herein, refers to antibody molecules in which amino acids have been replaced in the non-antigen binding regions in order to more closely resemble a human antibody, while still retaining the original binding ability.

THE INVENTION

Given the role C-type lectins play in regulating cell growth and development, the discovery of new molecules related to or in the C-type lectin gene family, and in the human reg/PSP multigene family in particular, is useful for developing diagnostic or therapeutic compositions directed at detecting or preventing neoplasia and/or metastasis. In addition, overexpression of PAP proteins is seen in acute pancreatitis and thus, novel human PAP genes are useful for developing diagnostic or therapeutic compositions directed at detection and treatment of pancreatitis and other disorders of the pancreas (e.g., pancreatic cell hyperplasia or hyperinsulinism).

As aberrant (e.g., ectopic) expression of members within the reg/PSP gene family is associated with tumorigenesis, the discovery of new molecules related to or in the reg/PSP gene family is useful for developing diagnostic or therapeutic compositions directed at a variety of tumors. Furthermore, new molecules related to or in the reg/PSP gene family are useful for developing diagnostic or therapeutic compositions directed at correcting diseases associated with the overexpression or underexpresssion of reg/PSP proteins.

The invention is based on the discovery of a novel human C-type lectin which is a member of the human reg/PSP multigene family integral membrane protein (human PAP-2), the polynucleotides encoding human PAP-2, and the use of these compositions for the diagnosis, prevention, or treatment of diseases associated with abnormal pancreatic tissue, including pancreatic tumors. In addition, as mRNA encoding human PAP-2 is found in a number of other tumors, human PAP-2 serves as a marker for cancerous cells, particularly esophageal, lung and intestinal (cecal and colon) tumor cells.

Nucleic acids encoding the human PAP-2 of the present invention were first identified in Incyte Clone 2072483 from the ISLTNOT01 cDNA library through a computer-generated search for amino acid sequence alignments. A consensus sequence, SEQ ID NO:2, was derived from the following overlapping and/or extended nucleic acid sequences: Incyte Clones 225534 (PANCNOT01), 227084 (PANCNOT01), 229613 (PANCNOT01) and 2072483 (ISLNOT01).

In one embodiment, the invention encompasses a polypeptide comprising the amino acid sequence of SEQ ID NO:1, as shown in FIGS. 1A and 1B. Human PAP-2 contains 175 amino acids, a number of which are residues shown to be conserved among mammalian PAP and Reg proteins and which are conserved among the CRD of C-type animal lectins. The conserved sequence motif found in C-type CRDs is described by Drickamer [Curr. Opin. Struc. Biol. (1993) 3:393]. Sequences corresponding to this conserved motif within the human PAP-2 of the present invention include $G_{48}$, $C_{68}$, $G_{105}$, $D_{108}$, $W_{133}$, $G_{144}$, $C_{146}$, $W_{158}$, $D_{160}$, $C_{163}$ and $C_{171}$. A version of this motif is found in the PROSITE database as the C-type lectin domain signature (CTL); residues 146–171 of SEQ ID NO:1 comprise the CTL listed in the PROSITE database.

Figure 2:
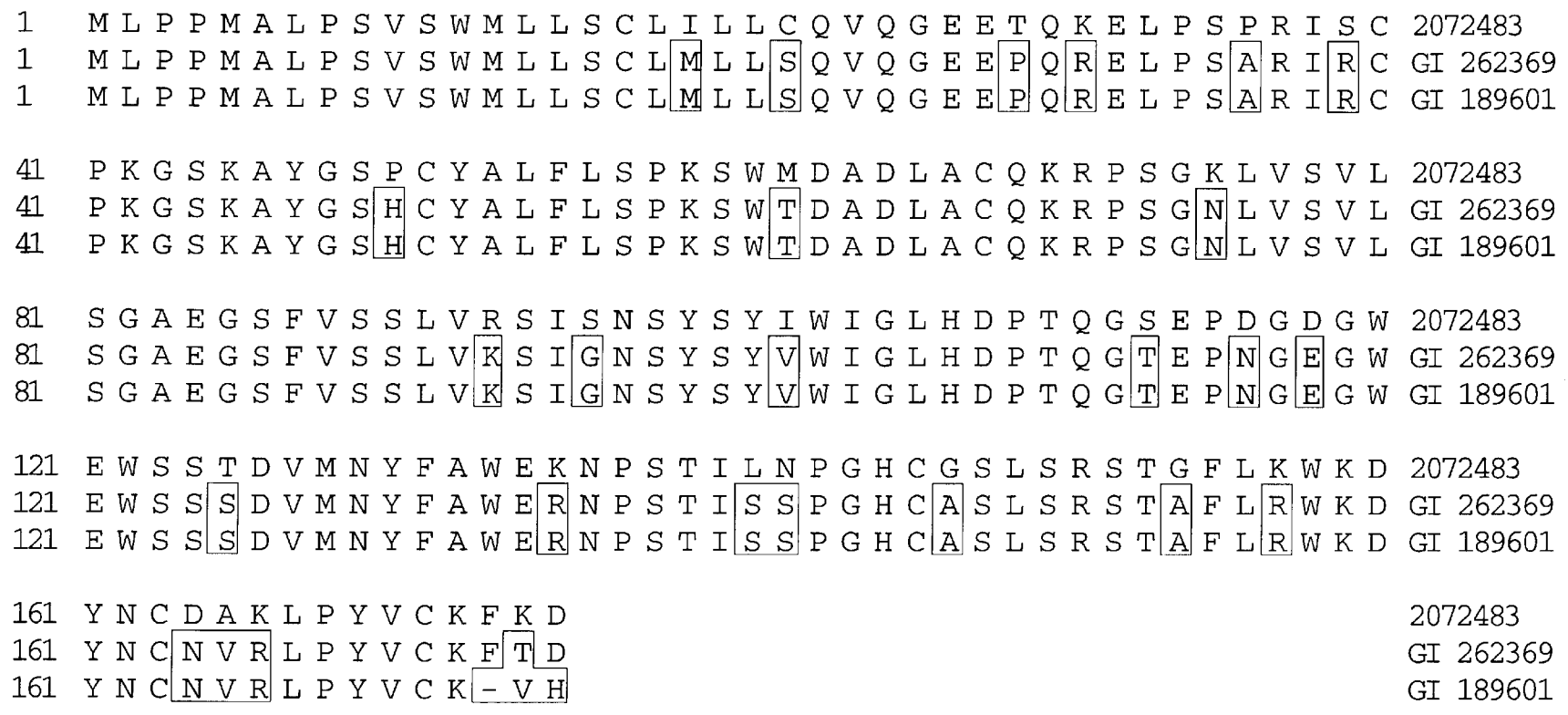

As shown in FIG. 2, human PAP-2 contains sequences that closely match the EGF-like domain cysteine pattern signature at residues 40–51 of SEQ ID NO:1. Human PAP-2 contains sequences that closely match the glucagon/GIP/secretin/VIP family signature consensus sequence (i.e., residues 82–104 of SEQ ID NO:1). Proteins within the glucagon/GIP/secretin/VIP family, like the PAP proteins including PAP-2, are expressed in the intestine or the pancreas.

The amino-terminal 26 residues of the human PAP-2 of the present invention comprise a putative signal sequence, a feature common to mammalian Reg and PAP proteins in general and to human and rat PAP I proteins in particular (Orelle et al., supra). The first amino acid of the mature or processed form of PAP-2 is therefore $E_{27}$ of SEQ ID NO:1.

Human PAP-2 contains eight cysteine residues (i.e., $C_{17}$, $C_{22}$, $C_{40}$ $C_{51}$, $C_{68}$, $C_{146}$, $C_{163}$, and $C_{171}$). In addition to providing sites for disulfide bond formation, the cysteine residues provide potential sites for palmitoylation. Seven of the eight cysteine residues found in human PAP-2 are conserved in location with cysteine residues found in the human PAP I (i.e., $C_{17}$, $C_{40}$, $C_{51}$, $C_{68}$, $C_{146}$, $C_{,163}$, and $C_{,171}$, of human PAP-2). The human PAP-2 of the present invention contains numerous potential O-linked glycosylation sites (i.e., serine and threonine residues). Human PAP-2 has a single potential N-linked glycoslyation site (i.e., Asn-X-Ser/Thr) (i.e., $N_{136}$) which is conserved in location with the single N-linked glycoslyation site found in the human PAP I protein. In addition, the human PAP-2 of the present invention contains numerous potential phosphorylation sites (i.e., typically the hydroxyl groups of serine, threonine and tyrosine residues although asparagine, histidine and lysine residues may also be phosphorylated), including two potential sites for phosphorylation by cAMP-dependent protein kinase (e.g., R-X-S/T) (i.e., $S_{73}$ and $T_{153}$); these sites are conserved in location with the two potential cAMP-dependent protein kinase phosphorylation sites found in the human PAP I protein.

Human PAP-2 has chemical and structural homology with the human PAP I protein (GI 262369; SEQ ID NO:3) (Orelle et al., supra). In particular, human PAP-2 and PAP I share 85% identity and 92% similarity. A pair of residues are said to be similar if they represent conservative substitutions. FIG. 2 provides an alignment between the amino acid sequences of SEQ ID NOS:1 and 3.

Figure 3B:
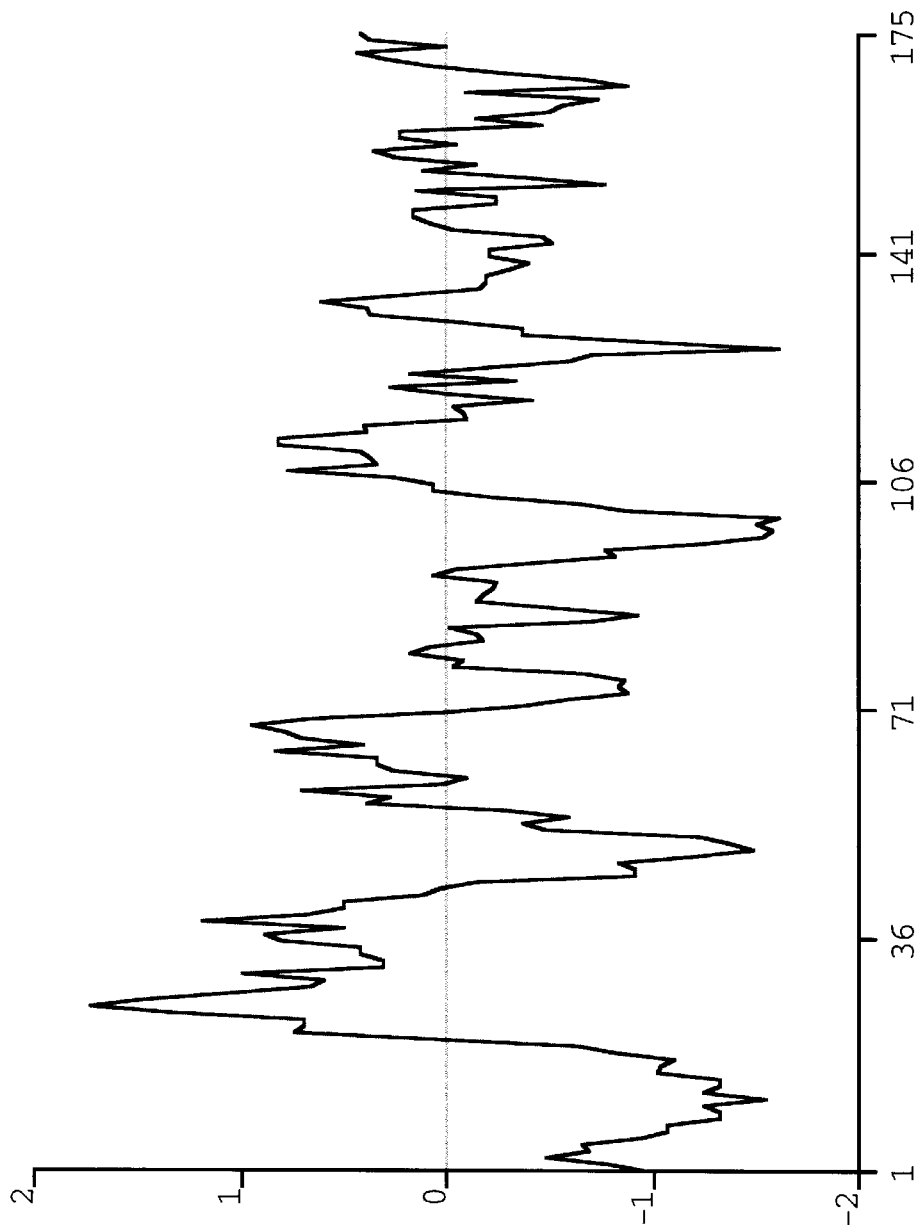

The human PAP-2 protein of the present invention, like the human PAP 1 protein (GI 262369), has a nearly neutral isoelectric point (pI) (human PAP-2 has a pI of 6.84 and PAP I has a pI of 7.54). As illustrated by FIGS. 3A and 3B, human PAP-2 and PAP I (GI 262369) have similar hydrophobicity plots.

Northern analysis (FIG. 4) shows the expression of human PAP-2-encoding sequences in various libraries, 25% of which are cancerous and 20% of which are involved with the immune response, including inflammatory and/or autoimmune disease (e.g., ulcerative colitis, Crohn's disease). Of particular note is the expression of human PAP-2 mRNA in pancreatic tumor (1/20), esophageal tumor (1/20), cecal tumor (1/20) and colon tumor (1/20) libraries. Human PAP-2, like other members of the reg/PSP multigene family, is expressed in the pancreas. Human PAP-2 is expressed at relatively high levels in apparently normal pancreatic tissue (i.e., tissue not identified as being tumorous or otherwise obviously diseased) while the expression of other PAP mRNAs (e.g., human, mouse and rat PAP 1) is reported to be low in normal pancreatic tissue and elevated during the acute phase of pancreatitis (Itoh and Teraoka, supra). Human PAP-2 is also expressed at relatively high levels in the small intestine, a feature in common with human, mouse and rat PAP I (Itoh and Teraoka, supra). Thus, human PAP-2 sequences serve as a marker for the small intestine, especially the ileum.

The invention also encompasses human PAP-2 variants. A preferred human PAP-2 variant is one having at least 86%, and more preferably 90%, amino acid sequence identity to the human PAP-2 amino acid sequence (SEQ ID NO:1). A most preferred human PAP-2 variant is one having at least 95% amino acid sequence identity to SEQ ID NO:1.

The invention also encompasses polynucleotides which encode human PAP-2. Accordingly, any nucleic acid sequence which encodes the amino acid sequence of human PAP-2 can be used to generate recombinant molecules which express human PAP-2. In a particular embodiment, the invention encompasses the polynucleotide comprising the nucleic acid sequence of SEQ ID NO:2 as shown in FIGS. 1A and 1B.

It will be appreciated by those skilled in the art that as a result of the degeneracy of the genetic code, a multitude of nucleotide sequences encoding human PAP-2, some bearing minimal homology to the nucleotide sequences of any known and naturally occurring gene, may be produced. Thus, the invention contemplates each and every possible variation of nucleotide sequence that could be made by selecting combinations based on possible codon choices. These combinations are made in accordance with the standard triplet genetic code as applied to the nucleotide sequence of naturally occurring human PAP-2, and all such variations are to be considered as being specifically disclosed.

Although nucleotide sequences which encode human PAP-2 and its variants are preferably capable of hybridizing to the nucleotide sequence of the naturally occurring human PAP-2 under appropriately selected conditions of stringency, it may be advantageous to produce nucleotide sequences encoding human PAP-2 or its derivatives possessing a substantially different codon usage. Codons may be selected to increase the rate at which expression of the peptide occurs in a particular prokaryotic or eukaryotic host in accordance with the frequency with which particular codons are utilized by the host. Other reasons for substantially altering the nucleotide sequence encoding human PAP-2 and its derivatives without altering the encoded amino acid sequences include the production of RNA transcripts having more desirable properties, such as a greater half-life, than transcripts produced from the naturally occurring sequence.

The invention also encompasses production of DNA sequences, or portions thereof, which encode human PAP-2 and its derivatives, entirely by synthetic chemistry. After production, the synthetic sequence may be inserted into any of the many available expression vectors and cell systems using reagents that are well known in the art at the time of the filing of this application. Moreover, synthetic chemistry may be used to introduce mutations into a sequence encoding IMP- or any portion thereof.

Also encompassed by the invention are polynucleotide sequences that are capable of hybridizing to the claimed nucleotide sequences, and in particular, those shown in SEQ ID NO:2, under various conditions of stringency. Hybridization conditions are based on the melting temperature (Tm) of the nucleic acid binding complex or probe, as taught in Wahl, G. M. and S. L. Berger (1987; Methods Enzymol. 152:399–407) and Kimmel, A. R. (1987; Methods Enzymol. 152:507–511), and may be used at a defined stringency.

Altered nucleic acid sequences encoding human PAP-2 which are encompassed by the invention include deletions, insertions, or substitutions of different nucleotides resulting in a polynucleotide that encodes the same or a functionally equivalent human PAP-2. The encoded protein may also contain deletions, insertions, or substitutions of amino acid residues which produce a silent change and result in a functionally equivalent human PAP-2. Deliberate amino acid substitutions may be made on the basis of similarity in polarity, charge, solubility, hydrophobicity, hydrophilicity, and/or the amphipathic nature of the residues as long as the biological activity of human PAP-2 is retained. For example, negatively charged amino acids may include aspartic acid and glutamic acid; positively charged amino acids may include lysine and arginine; and amino acids with uncharged polar head groups having similar hydrophilicity values may include leucine, isoleucine, and valine; glycine and alanine; asparagine and glutamine; serine and threonine; phenylalanine and tyrosine.

Also included within the scope of the present invention are alleles of the genes encoding human PAP-2. As used herein, an "allele" or "allelic sequence" is an alternative form of the gene which may result from at least one mutation in the nucleic acid sequence. Alleles may result in altered mRNAs or polypeptides whose structure or function may or may not be altered. Any given gene may have none, one, or many allelic forms. Common mutational changes which give rise to alleles are generally ascribed to natural deletions, additions, or substitutions of nucleotides. Each of these types of changes may occur alone, or in combination with the others, one or more times in a given sequence.

Methods for DNA sequencing which are well known and generally available in the art may be used to practice any embodiments of the invention. The methods may employ such enzymes as the Klenow fragment of DNA polymerase I, Sequenase® (US Biochemical Corp, Cleveland, Ohio), Taq polymerase (Perkin Elmer), thermostable T7 polymerase (Amersham, Chicago, Ill.), or combinations of recombinant polymerases and proofreading exonucleases such as the ELONGASE Amplification System marketed by Gibco BRL (Gaithersburg, Md.). Preferably, the process is automated with machines such as the Hamilton Micro Lab 2200 (Hamilton, Reno, Nev.), Peltier Thermal Cycler (PTC200; MJ Research, Watertown, Mass.) and the ABI 377 DNA sequencers (Perkin Elmer).

The nucleic acid sequences encoding human PAP-2 may be extended utilizing a partial nucleotide sequence and employing various methods known in the art to detect upstream sequences such as promoters and regulatory elements. For example, one method which may be employed, "restriction-site" PCR, uses universal primers to retrieve unknown sequence adjacent to a known locus (Sarkar, G. (1993) PCR Methods Applic. 2:318–322). In particular, genomic DNA is first amplified in the presence of primer to linker sequence and a primer specific to the known region. The amplified sequences are then subjected to a second round of PCR with the same linker primer and another specific primer internal to the first one. Products of each round of PCR are transcribed with an appropriate RNA polymerase and sequenced using reverse transcriptase.

Inverse PCR may also be used to amplify or extend sequences using divergent primers based on a known region (Triglia, T. et al. (1988) Nucleic Acids Res. 16:8186). The primers may be designed using OLIGO 4.06 Primer Analysis software (National Biosciences Inc., Plymouth, Minn.), or another appropriate program, to be 22–30 nucleotides in length, to have a GC content of 50% or more, and to anneal to the target sequence at temperatures about 68°–72° C. The method uses several restriction enzymes to generate a suitable fragment in the known region of a gene. The fragment is then circularized by intramolecular ligation and used as a PCR template.

Another method which may be used is capture PCR which involves PCR amplification of DNA fragments adjacent to a known sequence in human and yeast artificial chromosome DNA (Lagerstrom, M. et al. (1991) PCR Methods Applic. 1:111–119). In this method, multiple restriction enzyme digestions and ligations may also be used to place an engineered double-stranded sequence into an unknown portion of the DNA molecule before performing PCR.

Another method which may be used to retrieve unknown sequences is that of Parker, J. D. et al. (1991; Nucleic Acids Res. 19:3055–3060). Additionally, one may use PCR, nested primers, and PromoterFinder™ libraries to walk in genomic DNA (Clontech, Palo Alto, Calif.). This process avoids the need to screen libraries and is useful in finding intron/exon junctions.

When screening for full-length cDNAs, it is preferable to use libraries that have been size-selected to include larger cDNAs. Also, random-primed libraries are preferable, in that they will contain more sequences which contain the 5' regions of genes. Use of a randomly primed library may be especially preferable for situations in which an oligo d(T) library does not yield a full-length cDNA. Genomic libraries may be useful for extension of sequence into the 5' and 3' non-transcribed regulatory regions.

Capillary electrophoresis systems which are commercially available may be used to analyze the size or confirm the nucleotide sequence of sequencing or PCR products. In particular, capillary sequencing may employ flowable polymers for electrophoretic separation, four different fluorescent dyes (one for each nucleotide) which are laser activated, and detection of the emitted wavelengths by a charge coupled devise camera. Output/light intensity may be converted to electrical signal using appropriate software (e.g. Genotyper™ and Sequence Navigator™ Perkin Elmer) and the entire process from loading of samples to computer analysis and electronic data display may be computer controlled. Capillary electrophoresis is especially preferable for the sequencing of small pieces of DNA which might be present in limited amounts in a particular sample.

In another embodiment of the invention, polynucleotide sequences or fragments thereof which encode human PAP-2, or fusion proteins or functional equivalents thereof, may be used in recombinant DNA molecules to direct expression of human PAP-2 in appropriate host cells. Due to the inherent degeneracy of the genetic code, other DNA sequences which encode substantially the same or a functionally equivalent amino acid sequence may be produced and these sequences may be used to clone and express human PAP-2.

As will be understood by those of skill in the art, it may be advantageous to produce human PAP-2-encoding nucleotide sequences possessing non-naturally occurring codons. For example, codons preferred by a particular prokaryotic or eukaryotic host can be selected to increase the rate of protein expression or to produce a recombinant RNA transcript having desirable properties, such as a half-life which is longer than that of a transcript generated from the naturally occurring sequence.

The nucleotide sequences of the present invention can be engineered using methods generally known in the art in order to alter human PAP-2 encoding sequences for a variety of reasons, including but not limited to, alterations which modify the cloning, processing, and/or expression of the gene product. DNA shuffling by random fragmentation and PCR reassembly of gene fragments and synthetic oligonucleotides may be used to engineer the nucleotide sequences. For example, site-directed mutagenesis may be used to insert new restriction sites, alter glycosylation patterns, change codon preference, produce splice variants, or introduce mutations, and so forth.

In another embodiment of the invention, natural, modified, or recombinant nucleic acid sequences encoding human PAP-2 may be ligated to a heterologous sequence to encode a fusion protein. For example, to screen peptide libraries for inhibitors of human PAP-2 activity, it may be useful to encode a chimeric human PAP-2 protein that can be recognized by a commercially available antibody. A fusion protein may also be engineered to contain a cleavage site located between the human PAP-2 encoding sequence and the heterologous protein sequence, so that human PAP-2 may be cleaved and purified away from the heterologous moiety.

In another embodiment, sequences encoding human PAP-2 may be synthesized, in whole or in part, using chemical methods well known in the art (see Caruthers, M. H. et al. (1980) Nucl. Acids Res. Symp. Ser. 215–223, Horn, T. et al. (1980) Nucl. Acids Res. Symp. Ser. 225–232). Alternatively, the protein itself may be produced using chemical methods to synthesize the amino acid sequence of human PAP-2, or a portion thereof. For example, peptide synthesis can be performed using various solid-phase techniques (Roberge, J. Y. et al. (1995) Science 269:202–204) and automated synthesis may be achieved, for example, using the ABI 431A Peptide Synthesizer (Perkin Elmer).

The newly synthesized peptide may be substantially purified by preparative high performance liquid chromatography (e.g., Creighton, T. (1983) *Proteins, Structures and Molecular Principles*, WH Freeman and Co., New York, N.Y.). The composition of the synthetic peptides may be confirmed by amino acid analysis or sequencing (e.g., the Edman degradation procedure; Creighton, supra). Additionally, the amino acid sequence of human PAP-2, or any part thereof, may be altered during direct synthesis and/or combined using chemical methods with sequences from other proteins, or any part thereof, to produce a variant polypeptide.

In order to express a biologically active human PAP-2, the nucleotide sequences encoding human PAP-2 or functional equivalents, may be inserted into appropriate expression vector, i.e., a vector which contains the necessary elements for the transcription and translation of the inserted coding sequence.

Methods which are well known to those skilled in the art may be used to construct expression vectors containing sequences encoding human PAP-2 and appropriate transcriptional and translational control elements. These methods include in vitro recombinant DNA techniques, synthetic techniques, and in vivo genetic recombination. Such techniques are described in Sambrook, J. et al. (1989) *Molecular Cloning, A Laboratory Manual*, Cold Spring Harbor Press, Plainview, N.Y., and Ausubel, F. M. et al. (1989) *Current Protocols in Molecular Biology*, John Wiley & Sons, New York, N.Y.

A variety of expression vector/host systems may be utilized to contain and express sequences encoding human PAP-2. These include, but are not limited to, microorganisms such as bacteria transformed with recombinant bacteriophage, plasmid, or cosmid DNA expression vectors; yeast transformed with yeast expression vectors; insect cell systems infected with virus expression vectors (e.g., baculovirus); plant cell systems transformed with virus expression vectors (e.g., cauliflower mosaic virus, CaMV; tobacco mosaic virus, TMV) or with bacterial expression vectors (e.g., Ti or pBR322 plasmids); or animal cell systems.

The "control elements" or "regulatory sequences" are those non-translated regions of the vector—enhancers, promoters, 5' and 3' untranslated regions—which interact with host cellular proteins to carry out transcription and translation. Such elements may vary in their strength and specificity. Depending on the vector system and host utilized, any number of suitable transcription and translation elements, including constitutive and inducible promoters, may be used. For example, when cloning in bacterial systems, inducible promoters such as the hybrid lacZ promoter of the Bluescript® phagemid (Stratagene, LaJolla, Calif.) or pSport1™ plasmid (Gibco BRL) and the like may be used. The baculovirus polyhedrin promoter may be used in insect cells. Promoters or enhancers derived from the genomes of plant cells (e.g., heat shock, RUBISCO; and storage protein genes) or from plant viruses (e.g., viral promoters or leader sequences) may be cloned into the vector. In mammalian cell systems, promoters from mammalian genes or from mammalian viruses are preferable. If it is necessary to generate a cell line that contains multiple copies of the sequence encoding human PAP-2, vectors based on SV40 or EBV may be used with an appropriate selectable marker.

In bacterial systems, a number of expression vectors may be selected depending upon the use intended for human PAP-2. For example, when large quantities of human PAP-2 are needed for the induction of antibodies, vectors which direct high level expression of fusion proteins that are readily purified may be used. Such vectors include, but are not limited to, the multifunctional *E. coli* cloning and expression vectors such as Bluescript® (Stratagene), in which the sequence encoding human PAP-2 may be ligated into the vector in frame with sequences for the amino-terminal Met and the subsequent 7 residues of β-galactosidase so that a hybrid protein is produced; pIN vectors (Van Heeke, G. and S. M. Schuster (1989) J. Biol. Chem. 264:5503–5509); and the like. pGEX vectors (Promega, Madison, Wis.) may also be used to express foreign polypeptides as fusion proteins with glutathione S-transferase (GST). In general, such fusion proteins are soluble and can easily be purified from lysed cells by adsorption to glutathione-agarose beads followed by elution in the presence of free glutathione. Proteins made in such systems may be designed to include heparin, thrombin, or factor XA protease cleavage sites so that the cloned polypeptide of interest can be released from the GST moiety at will.

In the yeast, *Saccharomyces cerevisiae*, a number of vectors containing constitutive or inducible promoters such as alpha factor, alcohol oxidase, and PGH may be used. For reviews, see Ausubel et al. (supra) and Grant et al. (1987) Methods Enzymol. 153:516–544. In cases where plant expression vectors are used, the expression of sequences encoding human PAP-2 may be driven by any of a number of promoters. For example, viral promoters such as the 35S and 19S promoters of CaMV may be used alone or in combination with the omega leader sequence from TMV (Takamatsu, N. (1987) EMBO J. 6:307–311). Alternatively, plant promoters such as the small subunit of RUBISCO or heat shock promoters may be used (Coruzzi, G. et al. (1984) EMBO J. 3:1671–1680; Broglie, R. et al. (1984) Science 224:838–843; and Winter, J. et al. (1991) Results Probl. Cell Differ. 17:85–105). These constructs can be introduced into plant cells by direct DNA transformation or pathogen-mediated transfection. Such techniques are described in a number of generally available reviews (see, for example, Hobbs, S. or Murry, L. E. in McGraw Hill *Yearbook of Science and Technology* (1992) McGraw Hill, New York, N.Y.; pp. 191–196.

An insect system may also be used to express human PAP-2. For example, in one such system, *Autographa californica* nuclear polyhedrosis virus (AcNPV) is used as a vector to express foreign genes in *Spodoptera frugiperda* cells or in Trichoplusia larvae. The sequences encoding human PAP-2 may be cloned into a non-essential region of the virus, such as the polyhedrin gene, and placed under control of the polyhedrin promoter. Successful insertion of human PAP-2 will render the polyhedrin gene inactive and produce recombinant virus lacking coat protein. The recombinant viruses may then be used to infect, for example, *S. frugiperda* cells or Trichoplusia larvae in which human PAP-2 may be expressed (Engelhard, E. K. et al. (1994) Proc. Nat. Acad. Sci. 91:3224–3227).

In mammalian host cells, a number of viral-based expression systems may be utilized. In cases where an adenovirus is used as an expression vector, sequences encoding human PAP-2 may be ligated into an adenovirus transcription/translation complex consisting of the late promoter and tripartite leader sequence. Insertion in a non-essential E1 or E3 region of the viral genome may be used to obtain a viable virus which is capable of expressing human PAP-2 in infected host cells (Logan, J. and Shenk, T. (1984) Proc. Natl. Acad. Sci. 81:3655–3659). In addition, transcription enhancers, such as the Rous sarcoma virus (RSV) enhancer, may be used to increase expression in mammalian host cells.

Specific initiation signals may also be used to achieve more efficient translation of sequences encoding human PAP-2. Such signals include the ATG initiation codon and adjacent sequences. In cases where sequences encoding human PAP-2, its initiation codon, and upstream sequences are inserted into the appropriate expression vector, no additional transcriptional or translational control signals may be needed. However, in cases where only coding sequence, or a portion thereof, is inserted, exogenous translational control signals including the ATG initiation codon should be provided. Furthermore, the initiation codon should be in the correct reading frame to ensure translation of the entire insert. Exogenous translational elements and initiation codons may be of various origins, both natural and synthetic. The efficiency of expression may be enhanced by the inclusion of enhancers which are appropriate for the particular cell system which is used, such as those described in the literature (Scharf, D. et al. (1994) Results Probl. Cell Differ. 20:125–162).

In addition, a host cell strain may be chosen for its ability to modulate the expression of the inserted sequences or to process the expressed protein in the desired fashion. Such modifications of the polypeptide include, but are not limited to, acetylation, carboxylation, glycosylation, phosphorylation, lipidation, and acylation. Post-translational processing which cleaves a "prepro" form of the protein may also be used to facilitate correct insertion, folding and/or function. Different host cells such as CHO (ATCC CCL 61 and CRL 9618), HeLa (ATCC CCL 2), MDCK (ATCC CCL 34 and CRL 6253), HEK 293 (ATCC CRL 1573), WI-38 (ATCC CCL 75) (ATCC: American Type Culture Collection, Rockville, Md.), which have specific cellular machinery and characteristic mechanisms for such post-translational activities, may be chosen to ensure the correct modification and processing of the foreign protein.

For long-term, high-yield production of recombinant proteins, stable expression is preferred. For example, cell lines which stably express human PAP-2 may be transformed using expression vectors which may contain viral origins of replication and/or endogenous expression elements and a selectable marker gene on the same or on a separate vector. Following the introduction of the vector, cells may be allowed to grow for 1–2 days in an enriched media before they are switched to selective media. The purpose of the selectable marker is to confer resistance to selection, and its presence allows growth and recovery of cells which successfully express the introduced sequences. Resistant clones of stably transformed cells may be proliferated using tissue culture techniques appropriate to the cell type.

Any number of selection systems may be used to recover transformed cell lines. These include, but are not limited to, the herpes simplex virus thymidine kinase (Wigler, M. et al. (1977) Cell 11:223–32) and adenine phosphoribosyltransferase (Lowy, I. et al. (1980) Cell 22:817–23) genes which can be employed in $tk^-$ or $aprt^-$ cells, respectively. Also, antimetabolite, antibiotic or herbicide resistance can be used as the basis for selection; for example, dhfr which confers resistance to methotrexate (Wigler, M. et al. (1980) Proc. Natl. Acad. Sci. 77:3567–70); npt, which confers resistance to the aminoglycosides neomycin and G-418 (Colbere-Garapin, F. et al (1981) J. Mol. Biol. 150:1–14) and also or pat, which confer resistance to chlorsulfuron and phosphinotricin acetyltransferase, respectively (Murry, supra). Additional selectable genes have been described, for example, trpB, which allows cells to utilize indole in place of tryptophan, or hisD, which allows cells to utilize histinol in place of histidine (Hartman, S. C. and R. C. Mulligan (1988) Proc. Natl. Acad. Sci. 85:8047–51). Recently, the use of visible markers has gained popularity with such markers as anthocyanins, β glucuronidase and its substrate GUS, and luciferase and its substrate luciferin, being widely used not only to identify transformants, but also to quantify the amount of transient or stable protein expression attributable to a specific vector system (Rhodes, C. A. et al. (1995) Methods Mol. Biol. 55:121–131).

Although the presence/absence of marker gene expression suggests that the gene of interest is also present, its presence and expression may need to be confirmed. For example, if the sequence encoding human PAP-2 is inserted within a marker gene sequence, recombinant cells containing sequences encoding human PAP-2 can be identified by the absence of marker gene function. Alternatively, a marker gene can be placed in tandem with a sequence encoding human PAP-2 under the control of a single promoter. Expression of the marker gene in response to induction or selection usually indicates expression of the tandem gene as well.

Alternatively, host cells which contain the nucleic acid sequence encoding human PAP-2 and express human PAP-2 may be identified by a variety of procedures known to those of skill in the art. These procedures include, but are not limited to, DNA-DNA or DNA-RNA hybridizations and protein bioassay or immunoassay techniques which include membrane, solution, or chip based technologies for the detection and/or quantification of nucleic acid or protein.

The presence of polynucleotide sequences encoding human PAP-2 can be detected by DNA-DNA or DNA-RNA hybridization or amplification using probes or portions or fragments of polynucleotides encoding human PAP-2. Nucleic acid amplification based assays involve the use of oligonucleotides or oligomers based on the sequences encoding human PAP-2 to detect transformants containing DNA or RNA encoding human PAP-2. As used herein "oligonucleotides" or "oligomers" refer to a nucleic acid sequence of at least about 10 nucleotides and as many as about 60 nucleotides, preferably about 15 to 30 nucleotides, and more preferably about 20–25 nucleotides, which can be used as a probe or amplimer.

A variety of protocols for detecting and measuring the expression of human PAP-2, using either polyclonal or monoclonal antibodies specific for the protein are known in the art. Examples include enzyme-linked immunosorbent assay (ELISA), radioimmunoassay (RIA), and fluorescence activated cell sorting (FACS). A two-site, monoclonal-based inmunoassay utilizing monoclonal antibodies reactive to two non-interfering epitopes on human PAP-2 is preferred, but a competitive binding assay may be employed. These and other assays are described, among other places, in Hampton, R. et al. (1990; Serological Methods, a Laboratory Manual, APS Press, St Paul, Minn.) and Maddox, D. E. et al. (1983; J. Exp. Med. 158:1211–1216).

A wide variety of labels and conjugation techniques are known by those skilled in the art and may be used in various nucleic acid and amino acid assays. Means for producing labeled hybridization or PCR probes for detecting sequences related to polynucleotides encoding human PAP-2 include oligolabeling, nick translation, end-labeling or PCR amplification using a labeled nucleotide. Alternatively, the sequences encoding human PAP-2, or any portions thereof may be cloned into a vector for the production of an mRNA probe. Such vectors are known in the art, are commercially available, and may be used to synthesize RNA probes in vitro by addition of an appropriate RNA polymerase such as T7, T3, or SP6 and labeled nucleotides. These procedures may be conducted using a variety of commercially available kits (Pharmacia & Upjohn, (Kalamazoo, Mich.); Promega (Madison Wis.); and U.S. Biochemical Corp., Cleveland, Ohio). Suitable reporter molecules or labels, which may be used, include radionuclides, enzymes, fluorescent, chemiluminescent, or chromogenic agents as well as substrates, cofactors, inhibitors, magnetic particles, and the like.

Host cells transformed with nucleotide sequences encoding human PAP-2 may be cultured under conditions suitable for the expression and recovery of the protein from cell culture. The protein produced by a recombinant cell may be secreted or contained intracellularly depending on the sequence and/or the vector used. As will be understood by those of skill in the art, expression vectors containing polynucleotides which encode human PAP-2 may be designed to contain signal sequences which direct secretion of human PAP-2 through a prokaryotic or eukaryotic cell membrane. The signal sequence may be encoded by the expression vector (i.e., a heterologous signal sequence) or by a sequence encoding the naturally occurring PAP-2 signal sequence (i.e., sequences encoding amino acid residues 1–26 of SEQ ID NO:1).

Other recombinant constructions may be used to join sequences encoding human PAP-2 to nucleotide sequences encoding a polypeptide domain which will facilitate purification of soluble proteins. Such purification facilitating domains include, but are not limited to, metal chelating peptides such as histidine-tryptophan modules that allow purification on immobilized metals, protein A domains that allow purification on immobilized immunoglobulin, and the domain utilized in the FLAGS extension/affinity purification system (Immunex Corp., Seattle, Wash.). The inclusion of cleavable linker sequences such as those specific for Factor XA or enterokinase (Invitrogen, San Diego, Calif.) between the purification domain and human PAP-2 may be used to facilitate purification. One such expression vector provides for expression of a fusion protein containing human PAP-2 and a nucleic acid encoding 6 histidine residues preceding a thioredoxin or an enterokinase cleavage site. The histidine residues facilitate purification on IMIAC (immobilized metal ion affinity chromatography as described in Porath, J. et al. (1992, Prot. Exp. Purif. 3: 263–281) while the enterokinase cleavage site provides a means for purifying human PAP-2 from the fusion protein. A discussion of vectors which contain fusion proteins is provided in Kroll, D. J. et al. (1993; DNA Cell Biol. 12:441–453).

In addition to recombinant production, fragments of human PAP-2 may be produced by direct peptide synthesis using solid-phase techniques Merrifield J. (1963) J. Am. Chem. Soc. 85:2149–2154). Protein synthesis may be performed using manual techniques or by automation. Automated synthesis may be achieved, for example, using Applied Biosystems 431A Peptide Synthesizer (Perkin Elmer). Various fragments of human PAP-2 may be chemically synthesized separately and combined using chemical methods to produce the full length molecule.

THERAPEUTICS

Based on the chemical and structural homology among human PAP-2 (SEQ ID NO:1) and the human PAP I protein (SEQ ID NOs:3 and 4), human PAP-2 appears to be a member of the reg/PSP multigene family and in particular a member of the PAP branch of this family. Human PAP I (and rat PAP I, mouse PAP I and rat PAP III) have been shown to be expressed at high levels during the acute phase of pancreatitis and in normal small intestine. Based on the homology between human PAP-2 and human PAP I and the pattern of PAP-2 mRNA expression, human PAP-2 protein and nucleotide sequences are believed to serve as a marker of acute pancreatitis. Human PAP-2 also shares chemical and structural homology with rat PAP I; rat PAP I has been shown to have the ability to aggregate bacteria. Therefore, human PAP-2 may be used therapeutically to control bacterial proliferation, a frequent complication of pancreatitis. The ectopic expression of members of the reg/PSP multigene family, including the PAP genes, is associated with a variety of disease states [Watanabbe et al. (1990) J. Biol. Chem. 265:7432; Lasserre et al., supra]. Expression of human PAP I in adult liver is associated with liver cancer; human PAP I is not expressed in normal adult or fetal liver (Lasserre et al., supra). As shown herein, PAP-2 is expression in a variety of tumor types, including pancreatic, esophageal, lung, cecal and colon tumors. Therefore, inhibition of human PAP-2 expression (e.g., using antisense PAP-2 transcripts), particularly in tissues in which PAP-2 is normally absent or expressed at low levels (i.e., ectopic expression), may be therapeutic. The PAP-2 amino acid and nucleic acid sequences provided herein provide a means of producing therapeutic compounds for the treatment of disease states associated with altered PAP-2 expression.

Therefore, in one embodiment, human PAP-2 or a fragment or derivative thereof may be administered to a subject to control the bacterial proliferation associated with infections or conditions such as pancreatitis.

In another embodiment, a vector capable of expressing human PAP-2, or a fragment or a derivative thereof, may also be administered to a subject to treat the bacterial proliferation described above.

In another embodiment, human PAP-2 may be administered in combination with other conventional chemotherapeutic agents (including antimicrobial agents). The combination of therapeutic agents having different mechanisms of action will have synergystic effects allowing for the use of lower effective doses of each agent and lessening side effects.

In one aspect, agonists of human PAP-2 may be used to increase the activity of human PAP-2 in cells having reduced human PAP-2 levels. Antibodies which are specific for human PAP-2 may be used directly as an agonist, or indirectly as a targeting or delivery mechanism for bringing a pharmaceutical agent to cells or tissue which express human PAP-2.

In one embodiment, antagonists or inhibitors of human PAP-2 may be administered to a subject to treat or prevent tumors, particularly pancreatic, esophageal, lung, cecal and colon tumors as well as Crohn's disease and ulcerative colitis.

In another embodiment, a vector expressing antisense of the polynucleotide encoding human PAP-2 may be administered to a subject to treat or prevent tumors, particularly pancreatic, esophageal, lung, cecal and colon tumors as well as Crohn's disease and ulcerative colitis.

Antagonists or inhibitors of human PAP-2 may be produced using methods which are generally known in the art. In particular, purified human PAP-2 may be used to produce antibodies or to screen libraries of pharmaceutical agents to identify those which specifically bind human PAP-2.

Antibodies which are specific for human PAP-2 may be used directly as an antagonist, or indirectly as a targeting or delivery mechanism for bringing a pharmaceutical agent to cells or tissue which express human PAP-2. The antibodies may be generated using methods that are well known in the art. Such antibodies may include, but are not limited to, polyclonal, monoclonal, chimeric, single chain, Fab fragments, and fragments produced by a Fab expression library. Neutralizing antibodies, (i.e., those which reduce or abolish human PAP-2 activity) are especially preferred for therapeutic use.

For the production of antibodies, various hosts including goats, rabbits, rats, mice, humans, and others, may be immunized by injection with human PAP-2 or any fragment or oligopeptide thereof which has immunogenic properties. Depending on the host species, various adjuvants may be used to increase immunological response. Such adjuvants include, but are not limited to, Freund's, mineral gels such as aluminum hydroxide, and surface active substances such as lysolecithin, pluronic polyols, polyanions, peptides, oil emulsions, keyhole limpet hemocyanin, and dinitrophenol. Among adjuvants used in humans, BCG (bacilli Calmette-Guerin) and *Corynebacterium parvum* are especially preferable.

It is preferred that the peptides, fragments, or oligopeptides used to induce antibodies to human PAP-2 have an amino acid sequence consisting of at least five amino acids, and more preferably at least 10 amino acids. It is also preferable that they are identical to a portion of the amino acid sequence of the natural protein, and they may contain the entire amino acid sequence of a small, naturally occurring molecule. Short stretches of human PAP-2 amino acids may be fused with those of another protein such as keyhole limpet hemocyanin and antibody produced against the chimeric molecule.

Monoclonal antibodies to human PAP-2 may be prepared using any technique which provides for the production of antibody molecules by continuous cell lines in culture. These include, but are not limited to, the hybridoma technique, the human B-cell hybridoma technique, and the EBV-hybridoma technique (Kohler, G. et al. (1975) Nature 256:495–497; Kozbor, D. et al. (1985) J. Immunol. Methods 81:31–42; Cote, R. J. et al. (1983) Proc. Natl. Acad. Sci. 80:2026–2030; Cole, S. P. et al. (1984) Mol. Cell Biol. 62:109–120).

In addition, techniques developed for the production of "chimeric antibodies", the splicing of mouse antibody genes to human antibody genes to obtain a molecule with appropriate antigen specificity and biological activity can be used (Morrison, S. L. et al. (1984) Proc. Natl. Acad. Sci. 81:6851–6855; Neuberger, M. S. et al. (1984) Nature 312:604–608; Takeda, S. et al. (1985) Nature 314:452–454). Alternatively, techniques described for the production of single chain antibodies may be adapted, using methods known in the art, to produce human PAP-2-specific single chain antibodies. Antibodies with related specificity, but of distinct idiotypic composition, may be generated by chain shuffling from random combinatorial immunoglobin libraries (Burton D. R. (1991) Proc. Natl. Acad. Sci. 88:11120–3).

Antibodies may also be produced by inducing in vivo production in the lymphocyte population or by screening recombinant immunoglobulin libraries or panels of highly specific binding reagents as disclosed in the literature (Orlandi, R. et al. (1989) Proc. Natl. Acad. Sci. 86: 3833–3837; Winter, G. et al. (1991) Nature 349:293–299).

Antibody fragments which contain specific binding sites for human PAP-2 may also be generated. For example, such fragments include, but are not limited to, the F(ab')2 fragments which can be produced by pepsin digestion of the antibody molecule and the Fab fragments which can be generated by reducing the disulfide bridges of the F(ab')2 fragments. Alternatively, Fab expression libraries may be constructed to allow rapid and easy identification of monoclonal Fab fragments with the desired specificity (Huse, W. D. et al. (1989) Science 254:1275–1281).

Various immunoassays may be used for screening to identify antibodies having the desired specificity. Numerous protocols for competitive binding or immunoradiometric assays using either polyclonal or monoclonal antibodies with established specificities are well known in the art. Such immunoassays typically involve the measurement of complex formation between human PAP-2 and its specific antibody. A two-site, monoclonal-based inmunoassay utilizing monoclonal antibodies reactive to two non-interfering human PAP-2 epitopes is preferred, but a competitive binding assay may also be employed (Maddox, supra).

In another embodiment of the invention, the polynucleotides encoding human PAP-2, or any fragment thereof, or antisense molecules, may be used for therapeutic purposes. In one aspect, antisense to the polynucleotide encoding human PAP-2 may be used in situations in which it would be desirable to block the transcription of the mRNA. In particular, cells may be transformed with sequences complementary to polynucleotides encoding human PAP-2. Thus, antisense molecules may be used to modulate human PAP-2 activity, or to achieve regulation of gene function. Such technology is now well known in the art, and sense or antisense oligomers or larger fragments, can be designed from various locations along the coding or control regions of sequences encoding human PAP-2.

Expression vectors derived from retroviruses, adenovirus, herpes or vaccinia viruses, or from various bacterial plasmids may be used for delivery of nucleotide sequences to the targeted organ, tissue or cell population. Methods which are well known to those skilled in the art can be used to construct recombinant vectors which will express antisense molecules complementary to the polynucleotides of the gene encoding human PAP-2. These techniques are described both in Sambrook et al. (supra) and in Ausubel et al. (supra).

Genes encoding human PAP-2 can be turned off by transforming a cell or tissue with expression vectors which express high levels of a polynucleotide or fragment thereof which encodes human PAP-2. Such constructs may be used to introduce untranslatable sense or antisense sequences into a cell. Even in the absence of integration into the DNA, such vectors may continue to transcribe RNA molecules until they are disabled by endogenous nucleases. Transient expression may last for a month or more with a non-replicating vector and even longer if appropriate replication elements are part of the vector system.

As mentioned above, modifications of gene expression can be obtained by designing antisense molecules, DNA, RNA, or PNA, to the control regions of the gene encoding human PAP-2, i.e., the promoters, enhancers, and introns. Oligonucleotides derived from the transcription initiation site, e.g., between positions −10 and +10 from the start site, are preferred. Similarly, inhibition can be achieved using "triple helix" base-pairing methodology. Triple helix pairing is useful because it causes inhibition of the ability of the double helix to open sufficiently for the binding of polymerases, transcription factors, or regulatory molecules. Recent therapeutic advances using triplex DNA have been described in the literature (Gee, J. E. et al. (1994) In: Huber, B. E. and B. I. Carr, *Molecular and Immunologic Approaches*, Futura Publishing Co., Mt. Kisco, N.Y.). The antisense molecules may also be designed to block translation of mRNA by preventing the transcript from binding to ribosomes.

Ribozymes, enzymatic RNA molecules, may also be used to catalyze the specific cleavage of RNA. The mechanism of ribozyme action involves sequence-specific hybridization of the ribozyme molecule to complementary target RNA, followed by endonucleolytic cleavage. Examples which may be used include engineered hammerhead motif ribozyme molecules that can specifically and efficiently catalyze endonucleolytic cleavage of sequences encoding human PAP-2.

Specific ribozyme cleavage sites within any potential RNA target are initially identified by scanning the target molecule for ribozyme cleavage sites which include the following sequences: GUA, GUU, and GUC. Once identified, short RNA sequences of between 15 and 20 ribonucleotides corresponding to the region of the target gene containing the cleavage site may be evaluated for secondary structural features which may render the oligonucleotide inoperable. The suitability of candidate targets may also be evaluated by testing accessibility to hybridization with complementary oligonucleotides using ribonuclease protection assays.

Antisense molecules and ribozymes of the invention may be prepared by any method known in the art for the synthesis of nucleic acid molecules. These include techniques for chemically synthesizing oligonucleotides such as solid phase phosphoramidite chemical synthesis. Alternatively, RNA molecules may be generated by in vitro and in vivo transcription of DNA sequences encoding human PAP-2. Such DNA sequences may be incorporated into a wide variety of vectors with suitable RNA polymerase promoters such as T7 or SP6. Alternatively, these cDNA constructs that synthesize antisense RNA constitutively or inducibly can be introduced into cell lines, cells, or tissues.

RNA molecules may be modified to increase intracellular stability and half-life. Possible modifications include, but are not limited to, the addition of flanking sequences at the 5' and/or 3' ends of the molecule or the use of phosphorothioate or 2' O-methyl rather than phosphodiesterase linkages within the backbone of the molecule. This concept is inherent in the production of PNAs and can be extended in all of these molecules by the inclusion of nontraditional bases such as inosine, queosine, and wybutosine, as well as acetyl-, methyl-, thio-, and similarly modified forms of adenine, cytidine, guanine, thymine, and uridine which are not as easily recognized by endogenous endonucleases.

Many methods for introducing vectors into cells or tissues are available and equally suitable for use in vivo, in vitro, and ex vivo. For ex vivo therapy, vectors may be introduced into stem cells taken from the patient and clonally propagated for autologous transplant back into that same patient. Delivery by transfection and by liposome injections may be achieved using methods which are well known in the art.

Any of the therapeutic methods described above may be applied to any subject in need of such therapy, including, for example, mammals such as dogs, cats, cows, horses, rabbits, monkeys, and most preferably, humans.

An additional embodiment of the invention relates to the administration of a pharmaceutical composition, in conjunction with a pharmaceutically acceptable carrier, for any of the therapeutic effects discussed above. Such pharmaceutical compositions may consist of human PAP-2, antibodies to human PAP-2, mimetics, agonists, antagonists, or inhibitors of human PAP-2. The compositions may be administered alone or in combination with at least one other agent, such as stabilizing compound, which may be administered in any sterile, biocompatible pharmaceutical carrier, including, but not limited to, saline, buffered saline, dextrose, and water. The compositions may be administered to a patient alone, or in combination with other agents, drugs or hormones.

The pharmaceutical compositions utilized in this invention may be administered by any number of routes including, but not limited to, oral, intravenous, intramuscular, intraarterial, intramedullary, intrathecal, intraventricular, transdermal, subcutaneous, intraperitoneal, intranasal, enteral, topical, sublingual, or rectal means.

In addition to the active ingredients, these pharmaceutical compositions may contain suitable pharmaceutically-acceptable carriers comprising excipients and auxiliaries which facilitate processing of the active compounds into preparations which can be used pharmaceutically. Further details on techniques for formulation and administration may be found in the latest edition of Remington's Pharmaceutical Sciences (Maack Publishing Co., Easton, Pa.).

Pharmaceutical compositions for oral administration can be formulated using pharmaceutically acceptable carriers well known in the art in dosages suitable for oral administration. Such carriers enable the pharmaceutical compositions to be formulated as tablets, pills, dragees, capsules, liquids, gels, syrups, slurries, suspensions, and the like, for ingestion by the patient.

Pharmaceutical preparations for oral use can be obtained through combination of active compounds with solid excipient, optionally grinding a resulting mixture, and processing the mixture of granules, after adding suitable auxiliaries, if desired, to obtain tablets or dragee cores. Suitable excipients are carbohydrate or protein fillers, such as sugars, including lactose, sucrose, mannitol, or sorbitol; starch from corn, wheat, rice, potato, or other plants; cellulose, such as methyl cellulose, hydroxypropylmethyl-cellulose, or sodium carboxymethylcellulose; gums including arabic and tragacanth; and proteins such as gelatin and collagen. If desired, disintegrating or solubilizing agents may be added, such as the cross-linked polyvinyl pyrrolidone, agar, alginic acid, or a salt thereof, such as sodium alginate.

Dragee cores may be used in conjunction with suitable coatings, such as concentrated sugar solutions, which may also contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification or to characterize the quantity of active compound, i.e., dosage.

Pharmaceutical preparations which can be used orally include push-fit capsules made of gelatin, as well as soft, sealed capsules made of gelatin and a coating, such as glycerol or sorbitol. Push-fit capsules can contain active ingredients mixed with a filler or binders, such as lactose or starches, lubricants, such as talc or magnesium stearate, and, optionally, stabilizers. In soft capsules, the active compounds may be dissolved or suspended in suitable liquids, such as fatty oils, liquid, or liquid polyethylene glycol with or without stabilizers.

Pharmaceutical formulations suitable for parenteral administration may be formulated in aqueous solutions, preferably in physiologically compatible buffers such as Hanks's solution, Ringer's solution, or physiologically buffered saline. Aqueous injection suspensions may contain substances which increase the viscosity of the suspension, such as sodium carboxymethyl cellulose, sorbitol, or dextran. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Optionally, the suspension may also contain suitable stabilizers or agents which increase the solubility of the compounds to allow for the preparation of highly concentrated solutions.

For topical or nasal administration, penetrants appropriate to the particular barrier to be permeated are used in the formulation. Such penetrants are generally known in the art.

The pharmaceutical compositions of the present invention may be manufactured in a manner that is known in the art, e.g., by means of conventional mixing, dissolving, granulating, dragee-making, levigating, emulsifying, encapsulating, entrapping, or lyophilizing processes.

The pharmaceutical composition may be provided as a salt and can be formed with many acids, including but not limited to, hydrochloric, sulfuric, acetic, lactic, tartaric, malic, succinic, etc. Salts tend to be more soluble in aqueous or other protonic solvents than are the corresponding free base forms. In other cases, the preferred preparation may be a lyophilized powder which may contain any or all of the following: 1–50 mM histidine, 0.1%–2% sucrose, and 2–7% mannitol, at a pH range of 4.5 to 5.5, that is combined with buffer prior to use.

After pharmaceutical compositions have been prepared, they can be placed in an appropriate container and labeled for treatment of an indicated condition. For administration of human PAP-2, such labeling would include amount, frequency, and method of administration.

Pharmaceutical compositions suitable for use in the invention include compositions wherein the active ingredients are contained in an effective amount to achieve the intended purpose. The determination of an effective dose is well within the capability of those skilled in the art.

For any compound, the therapeutically effective dose can be estimated initially either in cell culture assays, e.g., of neoplastic cells, or in animal models, usually mice, rabbits, dogs, or pigs. The animal model may also be used to determine the appropriate concentration range and route of administration. Such information can then be used to determine useful doses and routes for administration in humans.

A therapeutically effective dose refers to that amount of active ingredient, for example human PAP-2 or fragments thereof, antibodies of human PAP-2, agonists, antagonists or inhibitors of human PAP-2, which ameliorates the symptoms or condition. Therapeutic efficacy and toxicity may be determined by standard pharmaceutical procedures in cell cultures or experimental animals, e.g., ED50 (the dose therapeutically effective in 50% of the population) and LD50 (the dose lethal to 50% of the population). The dose ratio between therapeutic and toxic effects is the therapeutic index, and it can be expressed as the ratio, LD50/ED50.

Pharmaceutical compositions which exhibit large therapeutic indices are preferred. The data obtained from cell culture assays and animal studies is used in formulating a range of dosage for human use. The dosage contained in such compositions is preferably within a range of circulating concentrations that include the ED50 with little or no toxicity. The dosage varies within this range depending upon the dosage form employed, sensitivity of the patient, and the route of administration.

The exact dosage will be determined by the practitioner, in light of factors related to the subject that requires treatment. Dosage and administration are adjusted to provide sufficient levels of the active moiety or to maintain the desired effect. Factors which may be taken into account include the severity of the disease state, general health of the subject, age, weight, and gender of the subject, diet, time and frequency of administration, drug combination(s), reaction sensitivities, and tolerance/response to therapy. Long-acting pharmaceutical compositions may be administered every 3 to 4 days, every week, or once every two weeks depending on half-life and clearance rate of the particular formulation.

Normal dosage amounts may vary from 0.1 to 100,000 micrograms, up to a total dose of about 1 g, depending upon the route of administration. Guidance as to particular dosages and methods of delivery is provided in the literature and generally available to practitioners in the art. Those skilled in the art will employ different formulations for nucleotides than for proteins or their inhibitors. Similarly, delivery of polynucleotides or polypeptides will be specific to particular cells, conditions, locations, etc.

DIAGNOSTICS

In another embodiment, antibodies which specifically bind human PAP-2 may be used for the diagnosis of conditions or diseases characterized by expression of human PAP-2, or in assays to monitor patients being treated with human PAP-2, agonists, antagonists or inhibitors. The antibodies useful for diagnostic purposes may be prepared in the same manner as those described above for therapeutics. Diagnostic assays for human PAP-2 include methods which utilize the antibody and a label to detect human PAP-2 in human body fluids or extracts of cells or tissues. The antibodies may be used with or without modification, and may be labeled by joining them, either covalently or non-covalently, with a reporter molecule. A wide variety of reporter molecules which are known in the art may be used, several of which are described above.

A variety of protocols including ELISA, RIA, and FACS for measuring human PAP-2 are known in the art and provide a basis for diagnosing altered or abnormal levels of human PAP-2 expression. Normal or standard values for human PAP-2 expression are established by combining body fluids or cell extracts taken from normal mammalian subjects, preferably human, with antibody to human PAP-2 under conditions suitable for complex formation The amount of standard complex formation may be quantified by various methods, but preferably by photometric, means. Quantities of human PAP-2 expressed in subject, control and disease, samples from biopsied tissues are compared with the standard values. Deviation between standard and subject values establishes the parameters for diagnosing disease.

In another embodiment of the invention, the polynucleotides encoding human PAP-2 is used for diagnostic purposes. The polynucleotides which may be used include oligonucleotide sequences, antisense RNA and DNA molecules, and PNAs. The polynucleotides may be used to detect and quantitate gene expression in biopsied tissues in which expression of human PAP-2 may be correlated with disease. The diagnostic assay may be used to distinguish between absence, presence, and excess expression of human PAP-2, and to monitor regulation of human PAP-2 levels during therapeutic intervention.

In one aspect, hybridization with PCR probes which are capable of detecting polynucleotide sequences, including genomic sequences, encoding human PAP-2 or closely related molecules, may be used to identify nucleic acid sequences which encode human PAP-2. The specificity of the probe, whether it is made from a highly specific region, e.g., 10 unique nucleotides in the 5' regulatory region, or a less specific region, e.g., especially in the 3' coding region, and the stringency of the hybridization or amplification (maximal, high, intermediate, or low) will determine whether the probe identifies only naturally occurring sequences encoding human PAP-2, alleles, or related sequences.

Probes may also be used for the detection of related sequences, and should preferably contain at least 50% of the nucleotides from any of the human PAP-2 encoding sequences. The hybridization probes of the subject invention may be DNA or RNA and derived from the nucleotide sequence of SEQ ID NO:2 or from genomic sequence including promoter, enhancer elements, and introns of the naturally occurring human PAP-2.

Means for producing specific hybridization probes for DNAs encoding human PAP-2 include the cloning of nucleic acid sequences encoding human PAP-2 or human PAP-2 derivatives into vectors for the production of mRNA probes. Such vectors are known in the art, commercially available, and may be used to synthesize RNA probes in vitro by means of the addition of the appropriate RNA polymerases and the appropriate labeled nucleotides. Hybridization probes may be labeled by a variety of reporter groups, for example, radionuclides such as 32P or 35S, or enzymatic labels, such as alkaline phosphatase coupled to the probe via avidin/biotin coupling systems, and the like.

Polynucleotide sequences encoding human PAP-2 may be used for the diagnosis of conditions or diseases which are associated with expression of human PAP-2. Examples of such conditions or diseases include cancers of the pancreas, esophagus, lung, colon and colon and Crohn's disease and ulcerative colitis. The polynucleotide sequences encoding human PAP-2 may be used in Southern or northern analysis, dot blot, or other membrane-based technologies; in PCR technologies; or in dip stick, pin, ELISA or chip assays utilizing fluids or tissues from patient biopsies to detect altered human PAP-2 expression. Such qualitative or quantitative methods are well known in the art.

In a particular aspect, the nucleotide sequences encoding human PAP-2 provide the basis for assays that detect activation or induction of various cancers, particularly those mentioned above; in addition the lack of expression of human PAP-2 may be detected using the human PAP-2-encoding nucleotide sequences disclosed herein. The nucleotide sequences encoding human PAP-2 may be labeled by standard methods, and added to a fluid or tissue sample from a patient under conditions suitable for the formation of hybridization complexes. After a suitable incubation period, the sample is washed and the signal is quantitated and compared with a standard value. If the amount of signal in the biopsied or extracted sample is significantly altered from that of a comparable control sample, the nucleotide sequences have hybridized with nucleotide sequences in the sample, and the presence of altered levels of nucleotide sequences encoding human PAP-2 in the sample indicates the presence of the associated disease. Such assays may also be used to evaluate the efficacy of a particular therapeutic treatment regimen in animal studies, in clinical trials, or in monitoring the treatment of an individual patient.

In order to provide a basis for the diagnosis of disease associated with expression of human PAP-2, a normal or standard profile for expression is established. This may be accomplished by combining body fluids or cell extracts taken from normal subjects, either animal or human, with a sequence, or a fragment thereof, which encodes human PAP-2, under conditions suitable for hybridization or amplification. Standard hybridization may be quantified by comparing the values obtained from normal subjects with those from an experiment where a known amount of a substantially purified polynucleotide is used. Standard values obtained from normal samples may be compared with values obtained from samples from patients who are symptomatic for disease. Deviation between standard and subject values is used to establish the presence of disease.

Once disease is established and a treatment protocol is initiated, hybridization assays may be repeated on a regular basis to evaluate whether the level of expression in the patient begins to approximate that which is observed in the normal patient. The results obtained from successive assays may be used to show the efficacy of treatment over a period ranging from several days to months.

With respect to cancer, the presence of a relatively low or a relatively high amount of transcript in biopsied tissue from an individual may indicate a predisposition for the development of the disease, or may provide a means for detecting the disease prior to the appearance of actual clinical symptoms. A more definitive diagnosis of this type may allow health professionals to employ preventative measures or aggressive treatment earlier thereby preventing the development or further progression of the cancer.

Additional diagnostic uses for oligonucleotides designed from the sequences encoding human PAP-2 may involve the use of PCR. Such oligomers may be chemically synthesized, generated enzymatically, or produced from a recombinant source. Oligomers will preferably consist of two nucleotide sequences, one with sense orientation (5'→3') and another with antisense (3'←5'), employed under optimized conditions for identification of a specific gene or condition. The same two oligomers, nested sets of oligomers, or even a degenerate pool of oligomers may be employed under less stringent conditions for detection and/or quantitation of closely related DNA or RNA sequences.

Methods which may also be used to quantitate the expression of human PAP-2 include radiolabeling or biotinylating nucleotides, coamplification of a control nucleic acid, and standard curves onto which the experimental results are interpolated (Melby, P. C. et al. (1993) J. Immunol. Methods, 159:235–244; Duplaa, C. et al. (1993) Anal. Biochem. 229–236). The speed of quantitation of multiple samples may be accelerated by running the assay in an ELISA format where the oligomer of interest is presented in various dilutions and a spectrophotometric or colorimetric response gives rapid quantitation.

In another embodiment of the invention, the nucleic acid sequences which encode human PAP-2 may also be used to generate hybridization probes which are useful for mapping the naturally occurring genomic sequence. The sequences may be mapped to a particular chromosome or to a specific region of the chromosome using well known techniques. Such techniques include FISH, FACS, or artificial chromosome constructions, such as yeast artificial chromosomes, bacterial artificial chromosomes, bacterial P1 constructions or single chromosome cDNA libraries as reviewed in Price, C. M. (1993) Blood Rev. 7:127–134, and Trask, B. J. (1991) Trends Genet. 7:149–154.

FISH (as described in Verma et al. (1988) *Human Chromosomes: A Manual of Basic Techniques*, Pergamon Press, New York, N.Y.) may be correlated with other physical chromosome mapping techniques and genetic map data. Examples of genetic map data can be found in the 1994 Genome Issue of Science (265:1981f). Correlation between the location of the gene encoding human PAP-2 on a physical chromosomal map and a specific disease, or predisposition to a specific disease, may help delimit the region of DNA associated with that genetic disease. The nucleotide sequences of the subject invention may be used to detect differences in gene sequences between normal, carrier, or affected individuals.

In situ hybridization of chromosomal preparations and physical mapping techniques such as linkage analysis using established chromosomal markers may be used for extending genetic maps. Often the placement of a gene on the chromosome of another mammalian species, such as mouse, may reveal associated markers even if the number or arm of a particular human chromosome is not known. New sequences can be assigned to chromosomal arms, or parts thereof, by physical mapping. This provides valuable information to investigators searching for disease genes using positional cloning or other gene discovery techniques. Once the disease or syndrome has been crudely localized by genetic linkage to a particular genomic region, for example, AT to 11q22-23 (Gatti, R. A. et al. (1988) Nature 336:577–580), any sequences mapping to that area may represent associated or regulatory genes for further investigation. The nucleotide sequence of the subject invention may also be used to detect differences in the chromosomal location due to translocation, inversion, etc. among normal, carrier, or affected individuals.

In another embodiment of the invention, human PAP-2, its catalytic or immunogenic fragments or oligopeptides thereof, can be used for screening libraries of compounds in any of a variety of drug screening techniques. The fragment employed in such screening may be free in solution, affixed to a solid support, borne on a cell surface, or located intracellularly. The formation of binding complexes, between human PAP-2 and the agent being tested, may be measured.

Another technique for drug screening which may be used provides for high throughput screening of compounds having suitable binding affinity to the protein of interest as described in published PCT application WO84/03564. In this method, as applied to human PAP-2 large numbers of different small test compounds are synthesized on a solid substrate, such as plastic pins or some other surface. The test compounds are reacted with human PAP-2, or fragments thereof, and washed. Bound human PAP-2 is then detected by methods well known in the art. Purified human PAP-2 can also be coated directly onto plates for use in the aforementioned drug screening techniques. Alternatively, non-neutralizing antibodies can be used to capture the peptide and immobilize it on a solid support.

In another embodiment, one may use competitive drug screening assays in which neutralizing antibodies capable of binding human PAP-2 specifically compete with a test compound for binding human PAP-2. In this manner, the antibodies can be used to detect the presence of any peptide which shares one or more antigenic determinants with human PAP-2.

In additional embodiments, the nucleotide sequences which encode human PAP-2 may be used in any molecular biology techniques that have yet to be developed, provided the new techniques rely on properties of nucleotide sequences that are currently known, including, but not limited to, such properties as the triplet genetic code and specific base pair interactions.

The examples below are provided to illustrate the subject invention and are not included for the purpose of limiting the invention.

EXAMPLES

I ISLTNOT01 cDNA Library Construction

The ISLTNOT01 cDNA library was constructed from total RNA isolated from microscopically normal pancreatic islet cells (specimen #A143, Pfizer, Inc., New York, N.Y.). The frozen tissue was homogenized and lysed using a Brinkmann Homogenizer Polytron PT-3000 (Brinkmann Instruments, Westbury, N.J.) in guanidinium isothiocyanate solution. The lysate was centrifuged over a 5.7 M CsCl cushion using an Beckman SW28 rotor in a Beckman L8-70M Ultracentrifuge (Beckman Instruments) for 18 hours at 25,000 rpm at ambient temperature. The RNA was extracted with acid phenol pH 4.7, precipitated using 0.3 M sodium acetate and 2.5 volumes of ethanol, resuspended in RNAse-free water, and DNase treated at 37° C. Extraction and precipitation were repeated. The mRNA was isolated with the Qiagen Oligotex kit (QIAGEN, Inc. Chatsworth, Calif.) and used to construct the cDNA library.

The mRNA was handled according to the recommended protocols in the SuperScript Plasmid System for cDNA Synthesis and Plasmid Cloning (Cat. #18248-013, Gibco/BRL, Gaithersburg, Md.). The cDNAs were fractionated on a Sepharose CL4B column (Cat. #275105-01; Pharmacia), and those cDNAs exceeding 400 bp were ligated into pINCY1. The plasmid pINCY1 was subsequently transformed into DH5a™ competent cells (Cat. #18258-012; Gibco/BRL).

II Isolation and Sequencing of cDNA clones

Plasmid DNA was released from the cells and purified using the REAL Prep 96 Plasmid Kit (Catalog #26173; QIAGEN, Inc.). This kit enabled the simultaneous purification of 96 samples in a 96-well block using multi-channel reagent dispensers. The recommended protocol was employed except for the following changes: 1) the bacteria were cultured in 1 ml of sterile Terrific Broth (Catalog #22711, Gibco/BRL) with carbenicillin at 25 mg/L and glycerol at 0.4%; 2) after inoculation, the cultures were incubated for 19 hours and at the end of incubation, the cells were lysed with 0.3 ml of lysis buffer; and 3) following isopropanol precipitation, the plasmid DNA pellet was resuspended in 0.1 ml of distilled water. After the last step in the protocol, samples were transferred to a 96-well block for storage at 4° C.

The cDNAs were sequenced by the method of Sanger et al. (1975, *J. Mol. Biol.* 94:441f), using a Hamilton Micro Lab 2200 (Hamilton, Reno, Nev.) in combination with Peltier Thermal Cyclers (PTC200 from MJ Research, Watertown, Mass.) and Applied Biosystems 377 DNA Sequencing Systems.

III Homology Searching of cDNA Clones and Their Deduced Proteins

The nucleotide sequences of the Sequence Listing or amino acid sequences deduced from them were used as query sequences against databases such as GenBank, SwissProt, BLOCKS, and Pima II. These databases which contain previously identified and annotated sequences were searched for regions of homology (similarity) using BLAST, which stands for Basic Local Alignment Search Tool (Altschul (1993) supra, Altschul (1990) supra).

BLAST produces alignments of both nucleotide and amino acid sequences to determine sequence similarity. Because of the local nature of the alignments, BLAST is especially useful in determining exact matches or in identifying homologs which may be of prokaryotic (bacterial) or eukaryotic (animal, fungal or plant) origin. Other algorithms such as the one described in Smith RF and TF Smith (1992; Protein Engineering 5:35–51), incorporated herein by reference, can be used when dealing with primary sequence patterns and secondary structure gap penalties. As disclosed in this application, the sequences have lengths of at least 49 nucleotides, and no more than 12% uncalled bases (where N is recorded rather than A, C, G, or T).

The BLAST approach, as detailed in Karlin and Altschul (supra) and incorporated herein by reference, searches for matches between a query sequence and a database sequence, to evaluate the statistical significance of any matches found, and to report only those matches which satisfy the user-selected threshold of significance. In this application, threshold was set at $10^{-25}$ for nucleotides and $10^{-14}$ for peptides.

Incyte nucleotide sequences were searched against the GenBank databases for primate (pri), rodent (rod), and mammalian sequences (mam), and deduced amino acid sequences from the same clones are searched against GenBank functional protein databases, mammalian (mamp), vertebrate (vrtp) and eukaryote (eukp), for homology. The relevant database for a particular match were reported as a GIxxx±tp (where xxx is pri, rod, etc and if present, p=peptide) as shown in Table 1. In column 3 of Table 1, the product score is calculated as follows: the % nucleotide or amino acid identity [between the query and reference sequences] in BLAST is multiplied by the % maximum possible BLAST score [based on the lengths of query and reference sequences] and then divided by 100. Where an Incyte Clone was homologous to several sequences, up to five matches were provided with their relevant scores. In an analogy to the hybridization procedures used in the laboratory, the electronic stringency for an exact match was set at 70, and the conservative lower limit for an exact match was set at approximately 40 (with 1–2% error due to uncalled bases). Column 4 provides the log-likelihood where the value reflects the log of (probability divided by threshold); column 5, the relevant GenBank release; and column 6, a GenBank description of the protein, or an edited version thereof. Some of the GenBank descriptions presented in the tables of this application were standardized with respect to abbreviations and spelling.

A comparison of the full-length and partial cDNA sequences and the deduced amino acid sequences corresponding to the human PAP-2 gene and human PAP-2 protein with known nucleotide and protein sequences in GenBank revealed that the full-length human PAP-2 cDNA and protein sequences (i.e., SEQ ID NOS:1 and 2) were unique (i.e., not previously identified). This search revealed that the human PAP-2 protein shared some homology with the human PAP I protein (SEQ ID NOS:3 and 4) as well as other mammalian PAP proteins (e.g., the mouse PAP I protein, rat PAP I, II and III proteins, and bovine PTP) as well as a number of mammalian reg/litostathine proteins.

IV Northern Analysis

Northern analysis is a laboratory technique used to detect the presence of a transcript of a gene and involves the hybridization of a labeled nucleotide sequence to a membrane on which RNAs from a particular cell type or tissue have been bound (Sambrook et al., supra).

Analogous computer techniques using BLAST (Altschul, S. F. 1993 and 1990, supra) are used to search for identical or related molecules in nucleotide databases such as GenBank or the LIFESEQ™ database (Incyte Pharmaceuticals). This analysis is much faster than multiple, membrane-based hybridizations. In addition, the sensitivity of the computer search can be modified to determine whether any particular match is categorized as exact or homologous.

The basis of the search is the product score which is defined as:

% sequence identity x % maximum BLAST score/100

The product score takes into account both the degree of similarity between two sequences and the length of the sequence match. For example, with a product score of 40, the match will be exact within a 1–2% error; and at 70, the match will be exact. Homologous molecules are usually identified by selecting those which show product scores between 15 and 40, although lower scores may identify related molecules.

The results of northern analysis are reported as a list of libraries in which the transcript encoding human PAP-2 occurs. Abundance and percent abundance are also reported. Abundance directly reflects the number of times a particular transcript is represented in a cDNA library, and percent abundance is abundance divided by the total number of sequences examined in the cDNA library.

Electronic northern analysis (FIG. 4) revealed that mRNA encoding human PAP-2 (SEQ ID NO:1) was present in libraries generated primarily from pancreatic and intestinal tissues. Thus, the expression pattern of PAP-2 is similar to that seen with other mammalian PAP proteins. Human PAP-2 cDNA is expressed in a variety of tumors, including pancreas, esophagus, lung, cecal and colon tumors. Human PAP-2 cDNA is also expressed in a number of tissues that are involved with inflammatory and/or autoimmune disease (e.g., ulcerative colitis, Crohn's disease).

V Extension of PAP-2-Encoding Polynucleotide Sequences

Full length human PAP-2-encoding nucleic acid sequence (SEQ ID NO:2) is used to design oligonucleotide primers for extending a partial nucleotide sequence to full length or for obtaining 5' or 3', intron or other control sequences from genomic libraries. One primer is synthesized to initiate extension in the antisense direction (XLR) and the other is synthesized to extend sequence in the sense direction (XLF). Primers are used to facilitate the extension of the known sequence "outward" generating amplicons containing new, unknown nucleotide sequence for the region of interest. The initial primers are designed from the cDNA using OLIGO 4.06 (National Biosciences), or another appropriate program, to be 22–30 nucleotides in length, to have a GC content of 50% or more, and to anneal to the target sequence at temperatures about 68°–72° C. Any stretch of nucleotides which would result in hairpin structures and primer-primer dimerizations is avoided.

The original, selected cDNA libraries, or a human genomic library are used to extend the sequence; the latter is most useful to obtain 5' upstream regions. If more extension is necessary or desired, additional sets of primers are designed to further extend the known region.

By following the instructions for the XL-PCR kit (Perkin Elmer) and thoroughly mixing the enzyme and reaction mix, high fidelity amplification is obtained. Beginning with 40 pmol of each primer and the recommended concentrations of all other components of the kit, PCR is performed using the Peltier Thermal Cycler (PTC200; M. J. Research, Watertown, Mass.) and the following parameters:

Step 1 94° C. for 1 min (initial denaturation)
Step 2 65° C. for 1 min
Step 3 68° C. for 6 min
Step 4 94° C. for 15 sec
Step 5 65° C. for 1 min
Step 6 68° C. for 7 min
Step 7 Repeat step 4–6 for 15 additional cycles
Step 8 94° C. for 15 sec
Step 9 65° C. for 1 min
Step 10 68° C. for 7:15 min
Step 11 Repeat step 8–10 for 12 cycles
Step 12 72° C. for 8 min
Step 13 4° C. (and holding)

A 5–10 µl aliquot of the reaction mixture is analyzed by electrophoresis on a low concentration (about 0.6–0.8%) agarose mini-gel to determine which reactions were successful in extending the sequence. Bands thought to contain the largest products are selected and removed from the gel. Further purification involves using a commercial gel extraction method such as QIAQuick™ (QIAGEN Inc., Chatsworth, Calif.). After recovery of the DNA, Klenow enzyme is used to trim single-stranded, nucleotide overhangs creating blunt ends which facilitate religation and cloning.

After ethanol precipitation, the products are redissolved in 13 µl of ligation buffer, 1 µl T4-DNA ligase (15 units) and 1 µl T4 polynucleotide kinase are added, and the mixture is incubated at room temperature for 2–3 hours or overnight at 16° C. Competent E. coli cells (in 40 µl of appropriate media) are transformed with 3 µl of ligation mixture and cultured in 80 µl of SOC medium (Sambrook et al., supra). After incubation for one hour at 37° C., the whole transformation mixture is plated on Luria Bertani (LB)-agar (Sambrook et al., supra) containing 2x Carb. The following day, several colonies are randomly picked from each plate and cultured in 150 µl of liquid LB/2x Carb medium placed in an individual well of an appropriate, commercially-available, sterile 96-well microtiter plate. The following day, 5 µl of each overnight culture is transferred into a non-sterile 96-well plate and after dilution 1:10 with water, 5 µl of each sample is transferred into a PCR array.

For PCR amplification, 18 µl of concentrated PCR reaction mix (3.3×) containing 4 units of rTth DNA polymerase, a vector primer, and one or both of the gene specific primers used for the extension reaction are added to each well. Amplification is performed using the following conditions:

Step 1 94° C. for 60 sec
Step 2 94° C. for 20 sec
Step 3 55° C. for 30 sec
Step 4 72° C. for 90 sec
Step 5 Repeat steps 2–4 for an additional 29 cycles
Step 6 72° C. for 180 sec
Step 7 4° C. (and holding)

Aliquots of the PCR reactions are run on agarose gels together with molecular weight markers. The sizes of the PCR products are compared to the original partial cDNAs, and appropriate clones are selected, ligated into plasmid, and sequenced.

VI Labeling and Use of Hybridization Probes

Hybridization probes derived from SEQ ID NO:2 are employed to screen cDNAs, genomic DNAs, or mRNAs. Although the labeling of oligonucleotides, consisting of about 20 base-pairs, is specifically described, essentially the same procedure is used with larger cDNA fragments. Oligonucleotides are designed using state-of-the-art software such as OLIGO 4.06 (National Biosciences), labeled by combining 50 pmol of each oligomer and 250 µCi of [$\gamma^{32}$P] adenosine triphosphate (Amersham) and T4 polynucleotide kinase (DuPont NEN® Boston, Mass.). The labeled oligonucleotides are substantially purified with Sephadex G-25 superfine resin column (Pharmacia & Upjohn). A portion containing $10^7$ counts per minute of each of the sense and antisense oligonucleotides is used in a typical membrane based hybridization analysis of human genomic DNA digested with one of the following endonucleases (Ase I, Bgl II, Eco RI, Pst I, Xba 1, or Pvu II; DuPont NEN®).

The DNA from each digest is fractionated on a 0.7 percent agarose gel and transferred to nylon membranes (Nytran Plus, Schleicher & Schuell, Durham, N.H.). Hybridization is carried out for 16 hours at 40° C. To remove nonspecific signals, blots are sequentially washed at room temperature under increasingly stringent conditions up to 0.1× saline sodium citrate and 0.5% sodium dodecyl sulfate. After XOMAT ART™ film (Kodak, Rochester, N.Y.) is exposed to the blots in a Phosphoimager cassette (Molecular Dynamics, Sunnyvale, Calif.) for several hours, hybridization patterns are compared visually.

VII Antisense Molecules

Antisense molecules or sequence complementary to the human PAP-2-encoding sequence, or any part thereof, is used to inhibit in vivo or in vitro expression of naturally occurring human PAP-2. Although use of antisense oligonucleotides, comprising about 20 base-pairs, is specifically described, essentially the same procedure is used with larger cDNA fragments. An oligonucleotide based on the coding sequences of human PAP-2, as shown in FIGS. 1A and 1B, is used to inhibit expression of naturally occurring human PAP-2. The complementary oligonucleotide is designed from the most unique 5' sequence as shown in FIGS. 1A and 1B and used either to inhibit transcription by preventing promoter binding to the upstream nontranslated sequence or translation of an human PAP-2-encoding transcript by preventing the ribosome from binding. Using an appropriate portion of the signal and 5' sequence of SEQ ID NO:2, an effective antisense oligonucleotide includes any 15–20 nucleotides spanning the region which translates into the signal or 5' coding sequence of the polypeptide as shown in FIGS. 1A and 1B.

VIII Expression of Human PAP-2

Expression of human PAP-2 is accomplished by subcloning the cDNAs into appropriate vectors and transforming the vectors into host cells. In this case, the vector, pSport (Gibco/BRL), is used to express human PAP-2 in *E. coli*. Upstream of the cloning site, this vector contains a promoter for β-galactosidase, followed by sequence containing the amino-terminal Met, and the subsequent seven residues of β-galactosidase. Immediately following these eight residues is a bacteriophage promoter useful for transcription and a linker containing a number of unique restriction sites.

Induction of an isolated, transformed bacterial strain with IPTG using standard methods produces a fusion protein which consists of the first eight residues of β-galactosidase, about 5 to 15 residues of linker, and the full length protein or fragments thereof. Sequences encoding human PAP-2 fusion proteins lacking the naturally occurring signal sequence at residues 1–26 of SEQ ID NO:1 are preferentially employed for the production of recombinant human PAP-2. The signal residues present on the pSport vector direct the secretion of human PAP-2 into the bacterial growth media which can be used directly in the following assays for activity.

IX Demonstration of Human PAP-2 Activity

Given the chemical and structural similarity between the human PAP-2 and the human and rat PAP I proteins as well as other members of the reg/PSP multigene family, human PAP-2 is presumed to be a C-type lectin and therefore capable of binding to carbohydrates. The ability of recombinant human PAP-2 to bind carbohydrates may be demonstrated by examining the ability of human PAP-2 to bind to affinity columns comprising carbohydrates (e.g., lactose, maltose, D-mannose, D-galactose, etc. which are available from Sigma Chemical Corp., St. Louis, Mo.) or by using the assay described by Christa et al. (1994), supra.

C-type lectins, including rat PAP I, are known to agglutinate bacteria. The ability of human PAP-2 to agglutinate bacteria is demonstrated using the assay described by Iovanna et al. [(1991), supra]. Briefly, bacteria (e.g., *E. coli* strains KH802 or JM101) are grown at 37° C. to stationary phase in L-broth. The bacteria are then collected by centrifugation and washed in PBS. The washed bacteria are resuspended in PBS containing 0.5 mM $CaCl_2$ ($PBS/CaCl_2$) and are placed in the wells of microtiter plates at a concentration of approximately $5 \times 10^7$ bacteria/200 µl $PBS/CaCl_2$. Human PAP-2 is then added at a variety of concentrations (e.g., 1 to 50 µg/ml) and the presence of macroscopic aggregation is monitored following a 3 hour incubation at 25° C. Concanavalin A and albumin at 50 µg/ml may be employed as positive and negative controls, respectively.

X Production of Human PAP-2 Specific Antibodies

Human PAP-2 that is substantially purified using PAGE electrophoresis (Sambrook, supra), or other purification techniques, is used to immunize rabbits and to produce antibodies using standard protocols. The amino acid sequence deduced from SEQ ID NO:2 is analyzed using DNASTAR software (DNASTAR Inc) to determine regions of high immunogenicity and a corresponding oligopolypeptide is synthesized and used to raise antibodies by means known to those of skill in the art. Selection of appropriate epitopes, such as those near the C-terminus or in hydrophilic regions, is described by Ausubel et al. (supra), and others.

Typically, the oligopeptides are 15 residues in length, synthesized using an Applied Biosystems Peptide Synthesizer Model 431A using fmoc-chemistry, and coupled to keyhole limpet hemocyanin (KLH, Sigma, St. Louis, Mo.) by reaction with N-maleimidobenzoyl-N-hydroxysuccinimide ester (MBS; Ausubel et al., supra). Rabbits are immunized with the oligopeptide-KLH complex in complete Freund's adjuvant. The resulting antisera are tested for antipeptide activity, for example, by binding the peptide to plastic, blocking with 1% BSA, reacting with rabbit antisera, washing, and reacting with radioiodinated, goat anti-rabbit IgG.

XI Purification of Naturally Occurring Human PAP-2 Using Specific Antibodies Naturally occurring or recombinant human PAP-2 is substantially purified by immunoaffinity chromatography using antibodies specific for human PAP-2. An immunoaffinity column is constructed by covalently coupling human PAP-2 antibody to an activated chromatographic resin, such as CnBr-activated Sepharose (Pharmacia & Upjohn). After the coupling, the resin is blocked and washed according to the manufacturer's instructions.

Media containing human PAP-2 is passed over the immunoaffinity column, and the column is washed under conditions that allow the preferential absorbance of human PAP-2 (e.g., high ionic strength buffers in the presence of detergent). The column is eluted under conditions that disrupt antibody/human PAP-2 binding (eg, a buffer of pH 2–3 or a high concentration of a chaotrope, such as urea or thiocyanate ion), and human PAP-2 is collected.

XII Identification of Molecules Which Interact with Human PAP-2

Human PAP-2 or biologically active fragments thereof are labeled with $^{125}$I Bolton-Hunter reagent (Bolton et al. (1973) Biochem. J. 133: 529). Candidate molecules previously arrayed in the wells of a multi-well plate are incubated with the labeled human PAP-2, washed and any wells with labeled human PAP-2 complex are assayed. Data obtained using different concentrations of human PAP-2 are used to calculate values for the number, affinity, and association of human PAP-2 with the candidate molecules.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in molecular biology or related fields are intended to be within the scope of the following claims.

---

What is claimed is:

1. An isolated and purified polynucleotide sequence encoding a polypeptide comprising the amino acid sequence of SEQ ID NO:1.

2. A composition comprising the polynucleotide sequence of claim 1 and a suitable carrier.

3. An isolated and purified polynucleotide sequence comprising SEQ ID NO:2.

4. An isolated and purified polynucleotide sequence which is completely complementary to SEQ ID NO:2.

5. A composition comprising the polynucleotide sequence of claim 4 and a suitable carrier.

6. An expression vector comprising the polynucleotide sequence of claim 1.

7. A host cell comprising the expression vector of claim 6.

8. A method for producing a polypeptide comprising the amino acid sequence of SEQ ID NO:1, the method comprising the steps of:

a) culturing the host cell of claim 7 under conditions suitable for the expression of the polypeptide; and b) recovering the polypeptide.

* * * * *

SEQUENCE LISTING (1) GENERAL INFORMATION:

(iii) NUMBER OF SEQUENCES: 6

(2) INFORMATION FOR SEQ ID NO:1:

(i) SEQUENCE CHARACTERISTICS:
      (A) LENGTH: 175 amino acids
      (B) TYPE: amino acid
      (C) STRANDEDNESS: single
      (D) TOPOLOGY: linear (vii) IMMEDIATE SOURCE:
      (A) LIBRARY: ISLTNOT01
      (B) CLONE: 2072483

(xi) SEQUENCE DESCRIPTION: SEQ ID NO:1:

```
Met Leu Pro Pro Met Ala Leu Pro Ser Val Ser Trp Met Leu Leu Ser
 1               5                  10                  15

Cys Leu Ile Leu Leu Cys Gln Val Gln Gly Glu Glu Thr Gln Lys Glu
                20                  25                  30

Leu Pro Ser Pro Arg Ile Ser Cys Pro Lys Gly Ser Lys Ala Tyr Gly
            35                  40                  45

Ser Pro Cys Tyr Ala Leu Phe Leu Ser Pro Lys Ser Trp Met Asp Ala
        50                  55                  60

Asp Leu Ala Cys Gln Lys Arg Pro Ser Gly Lys Leu Val Ser Val Leu
65                  70                  75                  80
```

```
Ser Gly Ala Glu Gly Ser Phe Val Ser Leu Val Arg Ser Ile Ser
                85                  90                  95

Asn Ser Tyr Ser Tyr Ile Trp Ile Gly Leu His Asp Pro Thr Gln Gly
            100                 105                 110

Ser Glu Pro Asp Gly Asp Gly Trp Glu Trp Ser Ser Thr Asp Val Met
        115                 120                 125

Asn Tyr Phe Ala Trp Glu Lys Asn Pro Ser Thr Ile Leu Asn Pro Gly
    130                 135                 140

His Cys Gly Ser Leu Ser Arg Ser Thr Gly Phe Leu Lys Trp Lys Asp
145                 150                 155                 160

Tyr Asn Cys Asp Ala Lys Leu Pro Tyr Val Cys Lys Phe Lys Asp
                165                 170                 175
```

(2) INFORMATION FOR SEQ ID NO:2:

(i) SEQUENCE CHARACTERISTICS:
        (A) LENGTH: 762 base pairs
        (B) TYPE: nucleic acid
        (C) STRANDEDNESS: single
        (D) TOPOLOGY: linear (vii) IMMEDIATE SOURCE:
        (A) LIBRARY: ISLTNOT01
        (B) CLONE: 2072483

(xi) SEQUENCE DESCRIPTION: SEQ ID NO:2:

```
AGTCCTAGGG GACTACAGAA GGAAAAAGAC AAGAGGCAGT AGGATATCTG TGTGTCCTCC      60
CGCTGACCAC ACTTCCTTTA GTGACCCGAT TGCCTCCTCA AGTCGCAGAC ACTATGCTGC     120
CTCCCATGGC CCTGCCCAGT GTGTCCTGGA TGCTGCTTTC CTGCCTCATT CTCCTGTGTC     180
AGGTTCAAGG TGAAGAAACC CAGAAGGAAC TGCCCTCTCC ACGGATCAGC TGTCCCAAAG     240
GCTCCAAGGC CTATGGCTCC CCCTGCTATG CCTTGTTTTT GTCACCAAAA TCCTGGATGG     300
ATGCAGATCT GGCTTGCCAG AAGCGGCCCT CTGGAAAACT GGTGTCTGTG CTCAGTGGGG     360
CTGAGGGATC CTTCGTGTCC TCCCTGGTGA GGAGCATTAG TAACAGCTAC TCATACATCT     420
GGATTGGGCT CCATGACCCC ACACAGGGCT CTGAGCCTGA TGGAGATGGA TGGGAGTGGA     480
GTAGCACTGA TGTGATGAAT TACTTTGCAT GGGAGAAAAA TCCCTCCACC ATCTTAAACC     540
CTGGCCACTG TGGGAGCCTG TCAAGAAGCA CAGGATTTCT GAAGTGGAAA GATTATAACT     600
GTGATGCAAA GTTACCCTAT GTCTGCAAGT TCAAGGACTA GGGCAGGTGG GAAGTCAGCA     660
GCCTCAGCTT GGCGTGCAGC TCATCATGGA CATGAGACCA GTGTGAAGAC TCACCCTGGA     720
AGAGAATATT CTCCCCAAAC TGCCCTACCT GACTACCTTG TA                       762
```

(2) INFORMATION FOR SEQ ID NO:3:

(i) SEQUENCE CHARACTERISTICS:
        (A) LENGTH: 175 amino acids
        (B) TYPE: amino acid
        (C) STRANDEDNESS: single
        (D) TOPOLOGY: linear (vii) IMMEDIATE SOURCE:
        (A) LIBRARY: GenBank
        (B) CLONE: 262369

(xi) SEQUENCE DESCRIPTION: SEQ ID NO:3:

```
Met Leu Pro Pro Met Ala Leu Pro Ser Val Ser Trp Met Leu Leu Ser
1               5                   10                  15

Cys Leu Met Leu Leu Ser Gln Val Gln Gly Glu Glu Pro Gln Arg Glu
            20                  25                  30
```

```
Leu Pro Ser Ala Arg Ile Arg Cys Pro Lys Gly Ser Lys Ala Tyr Gly
            35                  40                  45

Ser His Cys Tyr Ala Leu Phe Leu Ser Pro Lys Ser Trp Thr Asp Ala
 50                  55                  60

Asp Leu Ala Cys Gln Lys Arg Pro Ser Gly Asn Leu Val Ser Val Leu
 65                  70                  75                  80

Ser Gly Ala Glu Gly Ser Phe Val Ser Leu Val Lys Ser Ile Gly
                 85                  90                  95

Asn Ser Tyr Ser Tyr Val Trp Ile Gly Leu His Asp Pro Thr Gln Gly
                100                 105                 110

Thr Glu Pro Asn Gly Glu Gly Trp Glu Trp Ser Ser Ser Asp Val Met
            115                 120                 125

Asn Tyr Phe Ala Trp Glu Arg Asn Pro Ser Thr Ile Ser Ser Pro Gly
        130                 135                 140

His Cys Ala Ser Leu Ser Arg Ser Thr Ala Phe Leu Arg Trp Lys Asp
145                 150                 155                 160

Tyr Asn Cys Asn Val Arg Leu Pro Tyr Val Cys Lys Phe Thr Asp
                165                 170                 175
```

(2) INFORMATION FOR SEQ ID NO:4:

(i) SEQUENCE CHARACTERISTICS:
        (A) LENGTH: 174 amino acids
        (B) TYPE: amino acid
        (C) STRANDEDNESS: single
        (D) TOPOLOGY: linear (vii) IMMEDIATE SOURCE:
        (A) LIBRARY: GenBank
        (B) CLONE: 189601

(xi) SEQUENCE DESCRIPTION: SEQ ID NO:4:

```
Met Leu Pro Pro Met Ala Leu Pro Ser Val Ser Trp Met Leu Leu Ser
 1               5                  10                  15

Cys Leu Met Leu Leu Ser Gln Val Gln Gly Glu Glu Pro Gln Arg Glu
             20                  25                  30

Leu Pro Ser Ala Arg Ile Arg Cys Pro Lys Gly Ser Lys Ala Tyr Gly
            35                  40                  45

Ser His Cys Tyr Ala Leu Phe Leu Ser Pro Lys Ser Trp Thr Asp Ala
 50                  55                  60

Asp Leu Ala Cys Gln Lys Arg Pro Ser Gly Asn Leu Val Ser Val Leu
 65                  70                  75                  80

Ser Gly Ala Glu Gly Ser Phe Val Ser Leu Val Lys Ser Ile Gly
                 85                  90                  95

Asn Ser Tyr Ser Tyr Val Trp Ile Gly Leu His Asp Pro Thr Gln Gly
                100                 105                 110

Thr Glu Pro Asn Gly Glu Gly Trp Glu Trp Ser Ser Ser Asp Val Met
            115                 120                 125

Asn Tyr Phe Ala Trp Glu Arg Asn Pro Ser Thr Ile Ser Ser Pro Gly
        130                 135                 140

His Cys Ala Ser Leu Ser Arg Ser Thr Ala Phe Leu Arg Trp Lys Asp
145                 150                 155                 160

Tyr Asn Cys Asn Val Arg Leu Pro Tyr Val Cys Lys Val His
                165                 170
```

(2) INFORMATION FOR SEQ ID NO:5:

(i) SEQUENCE CHARACTERISTICS:
        (A) LENGTH: 797 base pairs
        (B) TYPE: nucleic acid
        (C) STRANDEDNESS: single
        (D) TOPOLOGY: linear (vii) IMMEDIATE SOURCE:
        (A) LIBRARY: GenBank
        (B) CLONE: 262368

(xi) SEQUENCE DESCRIPTION: SEQ ID NO:5:

```
CGGGAGAGTG ACTCCTGATT GCCTCCTCAA GTCGCAGACA CTATGCTGCC TCCCATGGCC      60

CTGCCCAGTG TATCTTGGAT GCTGCTTTCC TGCCTCATGC TGCTGTCTCA GGTTCAAGGT     120

GAAGAACCCC AGAGGGAACT GCCCTCTGCA CGGATCCGCT GTCCCAAAGG CTCCAAGGCC     180

TATGGCTCCC ACTGCTATGC CTTGTTTTTG TCACCAAAAT CCTGGACAGA TGCAGATCTG     240

GCCTGCCAGA AGCGGCCCTC TGGAAACCTG GTGTCTGTGC TCAGTGGGGC TGAGGGATCC     300

TTCGTGTCCT CCCTGGTGAA GAGCATTGGT AACAGCTACT CATACGTCTG GATTGGGCTC     360

CATGACCCCA CACAGGGCAC CGAGCCCAAT GGAGAAGGTT GGGAGTGGAG TAGCAGTGAT     420

GTGATGAATT ACTTTGCATG GGAGAGAAAT CCCTCCACCA TCTCAAGCCC CGGCCACTGT     480

GCGAGCCTGT CGAGAAGCAC AGCATTTCTG AGGTGGAAAG ATTATAACTG TAATGTGAGG     540

TTACCCTATG TCTGCAAGTT CACTGACTAG TGCAGGAGGG AAGTCAGCAG CCTGTGTTTG     600

GTGTGCAACT CATCATGGGC ATGAGACCAG TGTGAGGACT CACCCTGGAA GAGAATATTC     660

GCTTAATTCC CCCAACCTGA CCACCTCATT CTTATCTTTC TTCTGTTTCT TCCTCCCCGC     720

TAGTCATTTC AGTCTCTTCA TTTTGTCATA CGGCCTAAGG CTTTAAAGAG CAATAAAATT     780

TTTAGTCTGC AAAAAAA                                                   797
```

(2) INFORMATION FOR SEQ ID NO:6:

(i) SEQUENCE CHARACTERISTICS:
        (A) LENGTH: 798 base pairs
        (B) TYPE: nucleic acid
        (C) STRANDEDNESS: single
        (D) TOPOLOGY: linear (vii) IMMEDIATE SOURCE:
        (A) LIBRARY: GenBank
        (B) CLONE: 189600

(xi) SEQUENCE DESCRIPTION: SEQ ID NO:6:

```
CGGGAGAGTG ACTCCTGATT GCCTCCTCAA GTCGCAGACA CTATGCTGCC TCCCATGGCC      60

CTGCCCAGTG TATCTTGGAT GCTGCTTTCC TGCCTCATGC TGCTGTCTCA GGTTCAAGGT     120

GAAGAACCCC AGAGGGAACT GCCCTCTGCA CGGATCCGCT GTCCCAAAGG CTCCAAGGCC     180

TATGGCTCCC ACTGCTATGC CTTGTTTTTG TCACCAAAAT CCTGGACAGA TGCAGATCTG     240

GCCTGCCAGA AGCGGCCCTC TGGAAACCTG GTGTCTGTGC TCAGTGGGGC TGAGGGATCC     300

TTCGTGTCCT CCCTGGTGAA GAGCATTGGT AACAGCTACT CATACGTCTG GATTGGGCTC     360

CATGACCCCA CACAGGGCAC CGAGCCCAAT GGAGAAGGTT GGGAGTGGAG TAGCAGTGAT     420

GTGATGAATT ACTTTGCATG GGAGAGAAAT CCCTCCACCA TCTCAAGCCC CGGCCACTGT     480

GCGAGCCTGT CGAGAAGCAC AGCATTTCTG AGGTGGAAAG ATTATAACTG TAATGTGAGG     540

TTACCCTATG TCTGCAAAGT TCACTGACTA GTGCAGGAGG GAAGTCAGCA GCCTGTGTTT     600
```

```
-continued

GGTGTGCAAC TCATCATGGG CATGAGACCA GTGTGAGGAC TCACCCTGGA AGAGAATATT      660

CGCTTAATTC CCCCAACCTG ACCACCTCAT TCTTATCTTT CTTCTGTTTC TTCCTCCCCG      720

CTAGTCATTT CAGTCTCTTC ATTTTGTCAT ACGGCCTAAG GCTTTAAAGA GCAATAAAAT      780

TTTTAGTCTG CAAAAAAA                                                    798
```